(12) United States Patent
Ohta et al.

(10) Patent No.: US 10,617,304 B2
(45) Date of Patent: Apr. 14, 2020

(54) RADIOGRAPHY SYSTEM

(71) Applicant: FUJIFILM CORPORATION, Tokyo (JP)

(72) Inventors: Yasunori Ohta, Kanagawa-ken (JP); Naoyuki Nishino, Kanagawa-ken (JP); Haruyasu Nakatsugawa, Kanagawa-ken (JP); Naoto Iwakiri, Kanagawa-ken (JP); Kouichi Kitano, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 1251 days.

(21) Appl. No.: 14/290,367

(22) Filed: May 29, 2014

(65) Prior Publication Data

US 2014/0275954 A1    Sep. 18, 2014

Related U.S. Application Data

(63) Continuation of application No. PCT/JP2012/080884, filed on Nov. 29, 2012.

(30) Foreign Application Priority Data

Nov. 30, 2011    (JP) ................................ 2011-262835

(51) Int. Cl.
*A61B 5/00*    (2006.01)
*A61B 6/00*    (2006.01)
(Continued)

(52) U.S. Cl.
CPC ........ *A61B 5/0071* (2013.01); *A61B 1/00006* (2013.01); *A61B 6/465* (2013.01);
(Continued)

(58) Field of Classification Search
CPC combination set(s) only.
See application file for complete search history.

(56) References Cited

U.S. PATENT DOCUMENTS 6,659,947 B1 *  12/2003  Carter .................. A61B 5/0006
                                                              600/300
7,283,615 B2 *  10/2007  Morehead ............ A61B 6/4405
                                                              378/114
(Continued)

FOREIGN PATENT DOCUMENTS

JP        9-253083 A        9/1997
JP       11-285492 A       10/1999
(Continued)

OTHER PUBLICATIONS

Japanese Office Action dated Mar. 8, 2016, issued in corresponding Japanese Patent Application No. 2015-079749.
(Continued)

*Primary Examiner* — Bo Joseph Peng
(74) *Attorney, Agent, or Firm* — Birch, Stewart, Kolasch & Birch, LLP

(57) ABSTRACT

This radiography system has a switching processing unit that switches the device that controls a radiation source and a radiography device to a control device or a portable apparatus. In a case where penetrative imaging has started, the switching processing unit switches the device that controls the radiation source and the radiography device from the control device to the portable apparatus.

11 Claims, 17 Drawing Sheets

(51) Int. Cl.
*A61B 8/00* (2006.01)
*G06F 19/00* (2018.01)
*A61B 1/00* (2006.01)
*G16H 40/63* (2018.01)

(52) U.S. Cl.
CPC .............. *A61B 6/548* (2013.01); *A61B 6/56* (2013.01); *A61B 8/465* (2013.01); *A61B 8/54* (2013.01); *A61B 8/56* (2013.01); *A61B 8/565* (2013.01); *G06F 19/321* (2013.01); *G16H 40/63* (2018.01); *A61B 1/0005* (2013.01); *A61B 1/00016* (2013.01); *A61B 1/00039* (2013.01); *A61B 1/00045* (2013.01); *A61B 6/4233* (2013.01); *A61B 6/4283* (2013.01); *A61B 6/4405* (2013.01); *A61B 6/4464* (2013.01)

(56) References Cited

U.S. PATENT DOCUMENTS

| | | | | |
|---|---|---|---|---|
| 7,549,961 | B1* | 6/2009 | Hwang | A61B 8/14 600/440 |
| 2003/0009102 | A1* | 1/2003 | Quistgaard | A61B 5/0402 600/446 |
| 2006/0159367 | A1* | 7/2006 | Zeineh | G02B 21/365 382/276 |
| 2006/0255904 | A1* | 11/2006 | Danzer | A61B 6/00 340/5.2 |
| 2007/0073937 | A1* | 3/2007 | Feinberg | G06F 9/445 710/62 |
| 2008/0049901 | A1 | 2/2008 | Tamakoshi | |
| 2008/0299163 | A1* | 12/2008 | Haskin | A01N 25/34 424/411 |
| 2009/0196398 | A1 | 8/2009 | Ohara | |
| 2010/0027752 | A1 | 2/2010 | Matsumoto | |
| 2011/0291800 | A1* | 12/2011 | Butzine | A61B 6/544 340/8.1 |
| 2011/0306882 | A1* | 12/2011 | Hannon | A61B 6/4494 600/443 |
| 2012/0189099 | A1* | 7/2012 | Liu | A61B 6/4233 378/62 |
| 2013/0279657 | A1* | 10/2013 | Hiroike | A61B 6/4233 378/62 |

FOREIGN PATENT DOCUMENTS

| | | |
|---|---|---|
| JP | 2006-109990 A | 4/2006 |
| JP | 2007-061385 A | 3/2007 |
| JP | 2008-220 A | 1/2008 |
| JP | 2010-035606 A | 2/2010 |
| WO | WO 2005/096944 A1 | 10/2005 |
| WO | WO 2006/109551 A1 | 10/2006 |

OTHER PUBLICATIONS

International Search Report issued in PCT/JP2012/080884 dated Feb. 12, 2013.

* cited by examiner

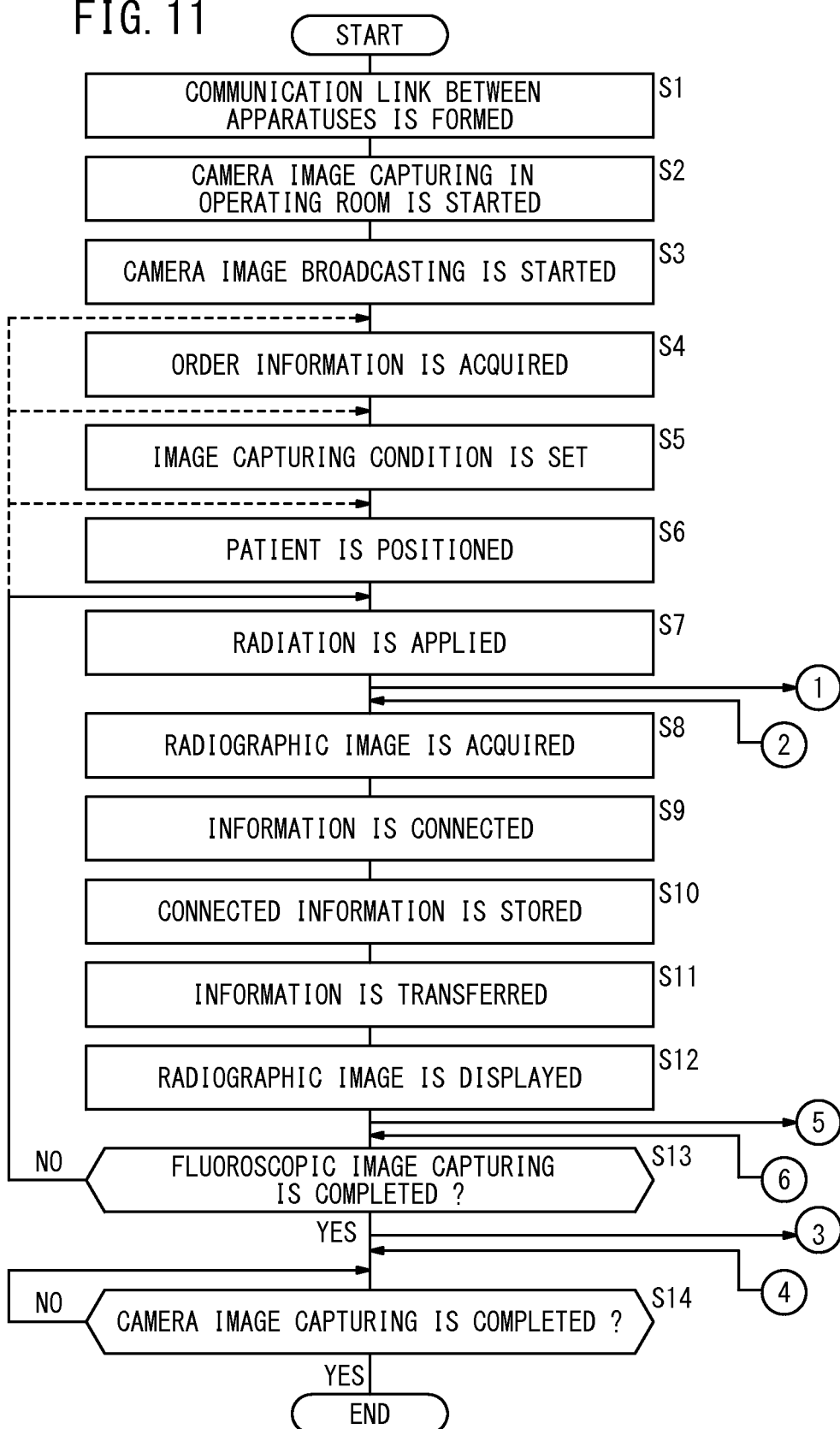

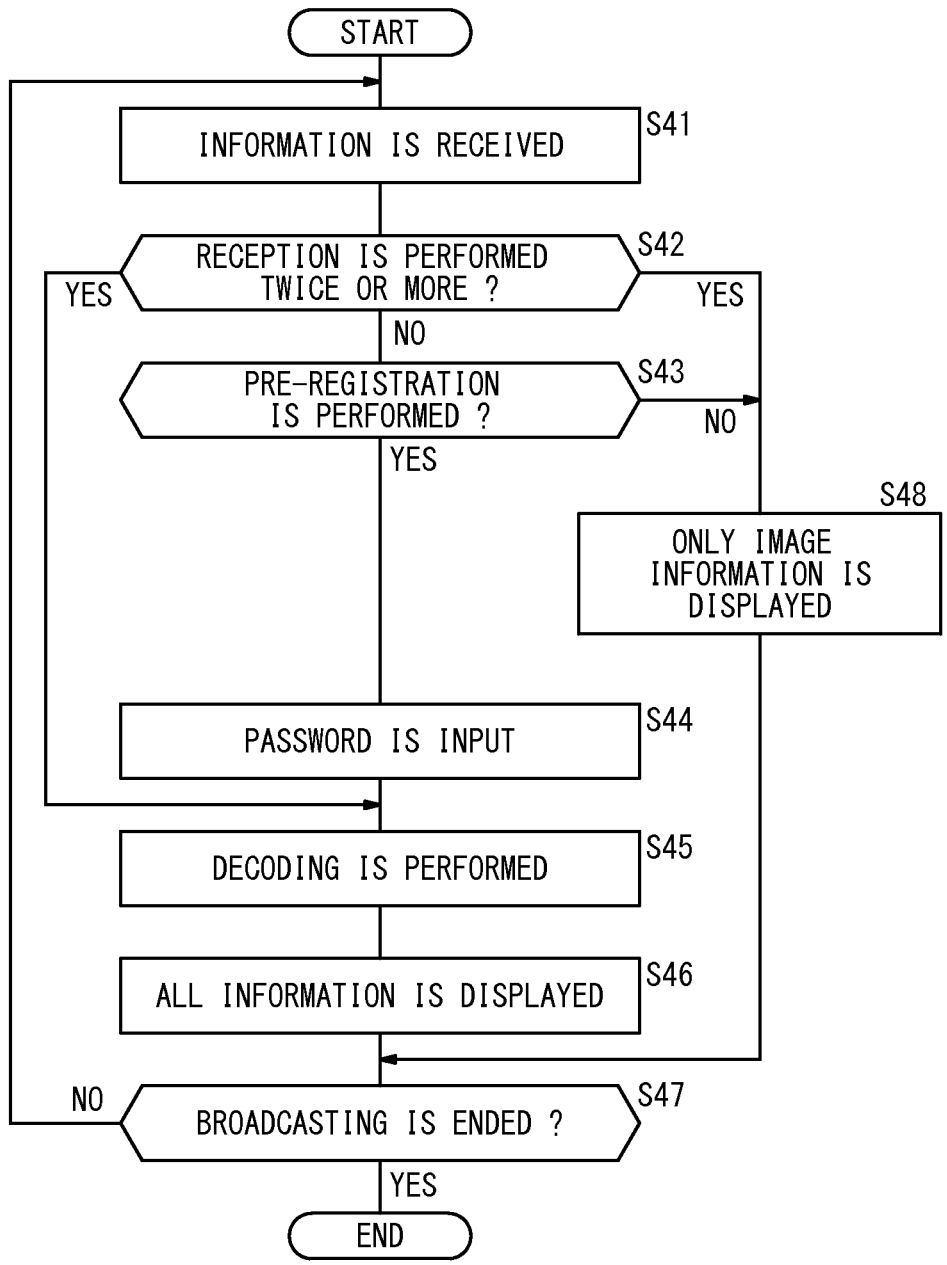

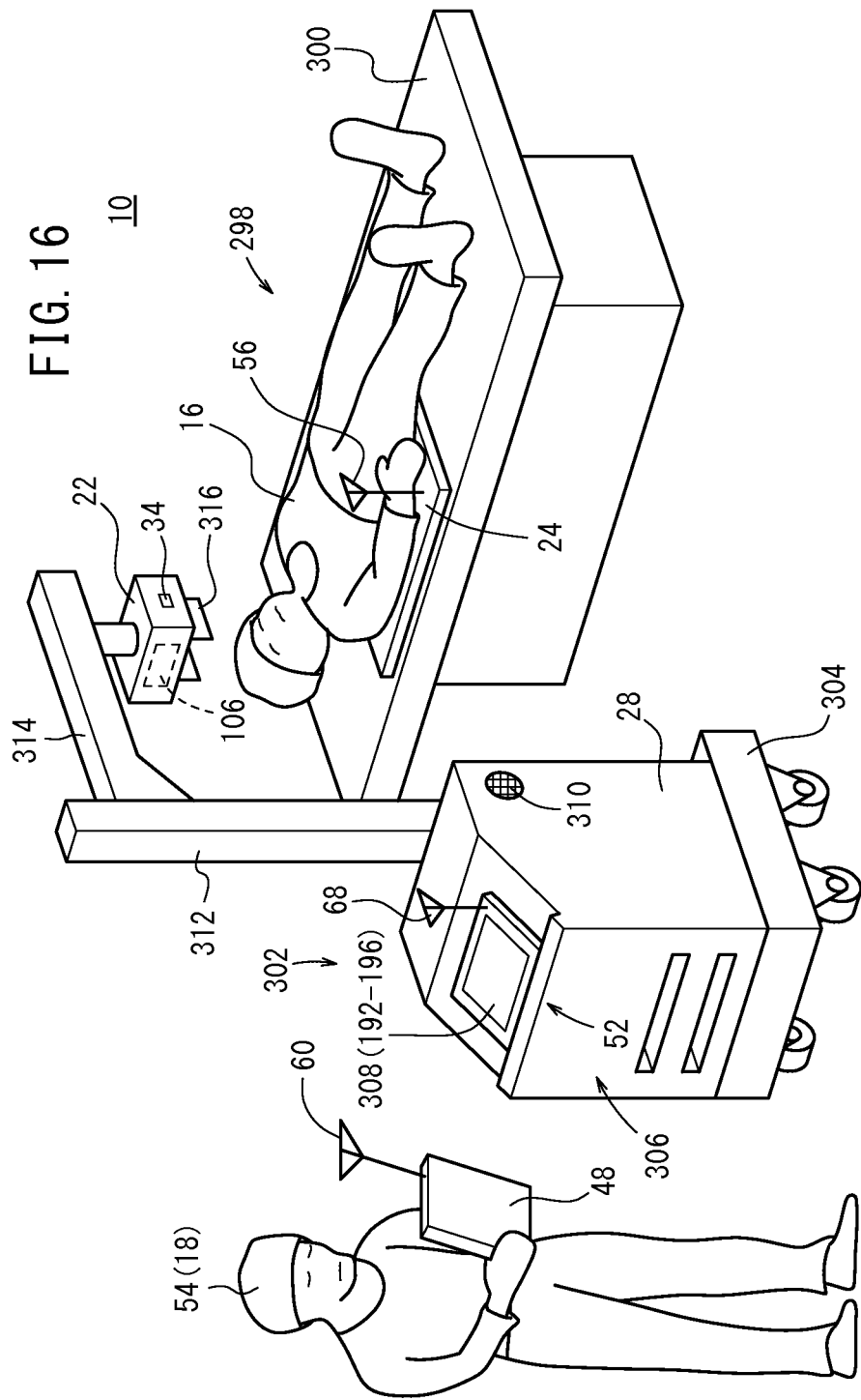

RADIOGRAPHY SYSTEM

CROSS-REFERENCE TO RELATED APPLICATIONS AND PRIORITY CLAIM

This application is a Continuation of International Application No. PCT/JP2012/080884 filed on Nov. 29, 2012, which was published under PCT Article 21(2) in Japanese, which is based upon and claims the benefit of priority from Japanese Patent Application No. 2011-262835 filed on Nov. 30, 2011, the contents all of which are incorporated herein by reference.

TECHNICAL FIELD

The present invention relates to a radiographic image capturing system capable of applying radiation to a subject and converting the radiation transmitted through the subject into a radiographic image.

BACKGROUND ART

Radiographic image capturing systems, which have a radiation source for applying radiation to a subject, a radiographic image capturing apparatus for converting the radiation transmitted through the subject into a radiographic image, and a control apparatus for controlling the radiation source and the radiographic image capturing apparatus, have been disclosed in Japanese Laid-Open Patent Publication No. 2010-035606, International Publication No. WO 2005/096944, International Publication No. WO 2006/109551, Japanese Laid-Open Patent Publication No. 2007-061385, Japanese Laid-Open Patent Publication No. 2006-109990, etc.

SUMMARY OF INVENTION

For example, in a case where the radiographic image capturing system disclosed in the related art documents is used in an operating room, a console is placed as the control apparatus in a position (preparation room) away from a patient of the subject. In this case, an operating doctor (surgeon) gives a verbal instruction to a radiologist, the radiologist operates the console based on the verbal instruction to set image capturing conditions and the like (including the tube voltage, tube current, and irradiation time of the radiation source) for the radiation application to the patient (the radiographic image capturing process), and the radiologist positions the patient around the radiation source and the radiographic image capturing apparatus. Then, the radiologist operates the console to start the radiographic image capturing process (such as a fluoroscopic process containing repeatedly applying the radiation to the patient to sequentially acquire radiographic images).

In a case where the radiographic image acquired in the fluorography is not clear to the doctor (e.g. because of the low contrast of the image or the body motion of the patient), the doctor verbally instructs the radiologist to interrupt the fluorography. The radiologist performs at least one of the changes (resetting) of the image capturing conditions and the positioning of the patient; and then restarts the fluorography.

However, the radiologist operates the console placed in the position away from the patient. Therefore, the radiologist may fail to appropriately change the image capturing conditions after he receives the verbal instruction from the doctor.

Furthermore, in a case where the radiologist performs the positioning of the patient, the radiologist moves from the console to the patient, performs the positioning of the patient, returns to the position of the console, and operates the console to restart the fluorography. Therefore, the radiologist's workload is increased, and the radiologist cannot rapidly complete a series of the procedures between the interruption and restart of the fluorography.

In a case where the doctor or the radiologist goes the rounds of the patients and performs the radiographic image capturing process using a round cart equipped with the console, the radiographic image capturing apparatus, and the like inside a medical institution, the doctor or the radiologist may change the image capturing conditions depending on the state of the patient. However, in a case where the radiographic image capturing apparatus is separated from the round cart, the positioning of the patient is performed, and then the image capturing conditions need to be changed depending on the state of the patient, the doctor or the radiologist moves to the patient, performs the positioning of the patient, returns to the console attached to the round cart, and then operates the console to change the image capturing conditions. Therefore, the doctor or the radiologist has to go back and forth between the patient and the round cart. Thus, the workload on the doctor or the radiologist is increased, and the procedures including the change of the image capturing conditions and the positioning of the subject cannot be rapidly performed.

The present invention has been made in view of the above drawbacks. It is an object of the present invention to provide a radiographic image capturing system capable of rapidly and appropriately performing the procedures including the change of the image capturing conditions and the positioning of the subject.

In view of the above object, a radiographic image capturing system according to the present invention comprises: a radiation source for applying radiation to a subject; a radiographic image capturing apparatus for converting the radiation transmitted through the subject into a radiographic image; a control apparatus for controlling the radiation source and the radiographic image capturing apparatus, disposed away from the subject; a mobile apparatus that can be moved close to the subject and can be used instead of the control apparatus for controlling the radiation source and the radiographic image capturing apparatus; and a switch processing portion for switching between the control apparatus and the mobile apparatus for controlling the radiation source and the radiographic image capturing apparatus.

In this structure, the control apparatus and the mobile apparatus are a master (main apparatus) and a slave (sub or subordinate apparatus) for controlling the radiation source and the radiographic image capturing apparatus. Therefore, the doctor or the radiologist can operate the switch processing portion to switch from the control apparatus to the mobile apparatus between the master and the slave, and can operate the switched master apparatus (the mobile apparatus) to reset (change) the image capturing conditions rapidly and appropriately. Furthermore, the doctor or the radiologist can operate the switched master apparatus (the mobile apparatus) to perform the procedures including the positioning of the subject rapidly and appropriately.

For example, in the case of using the radiographic image capturing system in an operating room, the radiographic image capturing system is preferably as follows.

In a case where the radiation is repeatedly applied to the subject by the radiation source and the radiographic images are sequentially acquired by the radiographic image capturing apparatus in fluorography, the apparatus for controlling the radiation source and the radiographic image capturing apparatus is switched from the control apparatus to the mobile apparatus by the switch processing portion.

In this case, the apparatus for controlling the radiation source and the radiographic image capturing apparatus is switched from the control apparatus to the mobile apparatus after the fluorography is started. Thus, the control apparatus and the mobile apparatus are the master and the slave for controlling the radiation source and the radiographic image capturing apparatus. Before the start of the fluorography, the control apparatus is the master, and the mobile apparatus is the slave. After the start of the fluorography, the control apparatus is switched to the slave, and the mobile apparatus is switched to the master.

Therefore, for example, the doctor (surgeon) can operate the switched master of the mobile apparatus placed in a position close to a patient as the subject (close to the doctor), and thereby can interrupt the fluorography and reset the image capturing conditions rapidly and appropriately without giving verbal instructions to the radiologist. In a case where the body of the patient is moved, the doctor gives a verbal instruction to the radiologist, and the radiologist performs only the positioning of the patient based on the instruction during the interruption of the fluorography. Consequently, the radiologist's workload can be reduced, and the positioning can be rapidly performed.

Thus, in the present invention, the procedures including the change of the image capturing conditions and the positioning of the subject can be rapidly and appropriately performed after the start of the fluorography, and the fluorography can be rapidly restarted after the interruption.

In a case where the apparatus (master) for controlling the radiation source and the radiographic image capturing apparatus is switched from the control apparatus to the mobile apparatus after the start of the fluorography as described above, the master is preferably switched from the mobile apparatus to the control apparatus by the switch processing portion after the end of the fluorography.

Therefore, after the end of the fluorography, the radiologist can operate the switched master of the control apparatus to set image capturing conditions for the next fluorography process. It is to be understood that the mobile apparatus is converted from the master to the slave by switching the control apparatus from the slave to the master.

In a case where the fluorography is interrupted, the mobile apparatus is preferably maintained as the master by the switch processing portion. Therefore, the doctor can operate the mobile apparatus during the interruption. Thus, before the end of the fluorography, the control apparatus is maintained as the slave.

In a case where the radiographic image capturing system further comprises a round cart, the radiographic image capturing system is preferably as follows.

In a case where at least the control apparatus and the mobile apparatus are disposed away from each other, the apparatus for controlling the radiation source and the radiographic image capturing apparatus is preferably switched from the control apparatus to the mobile apparatus by the switch processing portion.

Thus, in a case where the mobile apparatus is disposed away from at least the control apparatus, the master is preferably switched to the mobile apparatus. Therefore, for example, the operator (the doctor or the radiologist) can operate the mobile apparatus to change the image capturing conditions depending on the state of the subject while performing the positioning of the subject in a position close to the subject away from the control apparatus. Consequently, the operator does not need to go back and forth between the subject and the control apparatus in order to change the image capturing conditions, whereby the operator's workload can be reduced, and the procedures including the change of the image capturing conditions and the positioning of the subject can be rapidly performed.

Specifically, the radiographic image capturing system may further comprise a round cart for carrying at least the control apparatus, the mobile apparatus, and the radiographic image capturing apparatus. In a case where the mobile apparatus is separated from the round cart, the apparatus for controlling the radiation source and the radiographic image capturing apparatus is switched from the control apparatus to the mobile apparatus by the switch processing portion.

In this structure, in a case where the operator takes out the mobile apparatus from the round cart, the master is switched to the mobile apparatus. Therefore, for example, in a case where the operator moves away from the round cart to perform the positioning of the subject, the operator can operate the mobile apparatus to efficiently perform the change of the image capturing conditions and the control of the radiation source and the radiographic image capturing apparatus.

In this structure, in or after the positioning of the subject around the radiation source and the radiographic image capturing apparatus, the apparatus for controlling the radiation source and the radiographic image capturing apparatus may be switched from the control apparatus to the mobile apparatus by the switch processing portion.

In a case where the master is switched to the mobile apparatus in the step of the positioning of the subject, the image capturing conditions can be efficiently changed. In a case where the master is switched to the mobile apparatus after the positioning of the subject, the operator can use the mobile apparatus to remotely operate the radiation source and the radiographic image capturing apparatus, and the operator can be prevented from being exposed.

In the present invention, the mobile apparatus, the switch processing portion, and the radiographic image capturing apparatus are preferably as follows.

The mobile apparatus preferably contains a touch panel, and the operator (the doctor or the radiologist) preferably operates the touch panel to control the radiation source and the radiographic image capturing apparatus. Therefore, the operator can operate the touch panel to easily reset the image capturing conditions.

The touch panel for the operator does not have a concave-convex surface. Therefore, for example, the touch panel surface may be subjected to a sterilization treatment after a surgical operation, to keep the surface clean and to prevent in-hospital infection.

The mobile apparatus is preferably a tablet computer, a handheld computer, or a personal digital assistant. This type of the mobile apparatus can be easily carried close to the patient.

In particular, the tablet computer does not have a keyboard, a mouse, and the like, and does not have a concave-convex surface. Therefore, for example, the tablet computer surface may be subjected to a sterilization treatment after a surgical operation, to keep the surface clean and to prevent in-hospital infection.

The mobile apparatus is preferably sealed in a sterilized bag and used in this state. In this case, the operator touches the sterilized bag to operate the mobile apparatus, whereby the mobile apparatus can be kept clean. The sterilized bag may be a disposable transparent bag.

The switch processing portion may be formed on at least one of the control apparatus and the mobile apparatus, and the control apparatus and the mobile apparatus may send signals to and receive signals from each other. Therefore, the master and the slave can be rapidly switched between the control apparatus and the mobile apparatus. Furthermore, in a case where the mobile apparatus is the master, the mobile apparatus can control the radiation source and the radiographic image capturing apparatus using the control apparatus as a transponder.

The radiographic image capturing apparatus preferably contains a first communication portion for sending signals to and receiving signals from the control apparatus via a wired communication link, a second communication portion for sending signals to and receiving signals from the mobile apparatus via a wireless communication link, and an image processing portion for subjecting the radiographic image to a thinning (decimating) processing to generate a thinned image. The first communication portion preferably sends the radiographic image to the control apparatus, and the second communication portion preferably sends the thinned image to the mobile apparatus.

The generated thinned image has a smaller data amount (is formed at a lower frame rate with a smaller information amount) as compared with the radiographic image. Therefore, a moving image (the thinned image) can be sent from the radiographic image capturing apparatus to the mobile apparatus via the wireless communication link. Consequently, the thinned image can be rapidly displayed on a screen of the mobile apparatus. Furthermore, the original radiographic image can be sent from the radiographic image capturing apparatus to the control apparatus via the wired communication link without the thinning processing. Therefore, the radiographic image can be displayed on the screen of the control apparatus, and the original radiographic image can be stored in a memory or the like of the control apparatus. In addition, in a case where the control apparatus is used as the master, the control apparatus can directly control the radiographic image capturing apparatus via the first communication portion. On the other hand, in a case where the mobile apparatus is used as the master, the mobile apparatus can directly control the radiographic image capturing apparatus via the second communication portion.

The radiographic image capturing apparatus preferably further contains an image storage portion for storing the radiographic image. In a case where there is a defect in the signal sending and receiving between the first communication portion and the control apparatus via the wired communication link, the image storage portion preferably stores the radiographic image. Thus, even in a case where the original radiographic image that has not been thinned cannot be stored in the memory or the like of the control apparatus due to the defect in the signal transmission/reception via the wired communication link, the original radiographic image can be reliably stored in the image storage portion. Furthermore, the original radiographic image can be sent from the radiographic image capturing apparatus through the mobile apparatus to the control apparatus via the wireless communication link. In a case where the defect of the signal transmission/reception via the wired communication link is not eliminated even after switching the master to the control apparatus, the control apparatus can control the radiographic image capturing apparatus using the mobile apparatus as a transponder.

BRIEF DESCRIPTION OF DRAWINGS

FIG. 11 is a flowchart for illustrating the operation of the medical system of this embodiment;

FIG. 14 is a flowchart for illustrating the third specific function;

FIG. 16 is a perspective view for illustrating a second modification of this embodiment.

DESCRIPTION OF EMBODIMENTS

A preferred embodiment of the radiographic image capturing system of the present invention will be described in detail below with reference to FIGS. 1 to 17.

Configuration of Embodiment

Figure 1:
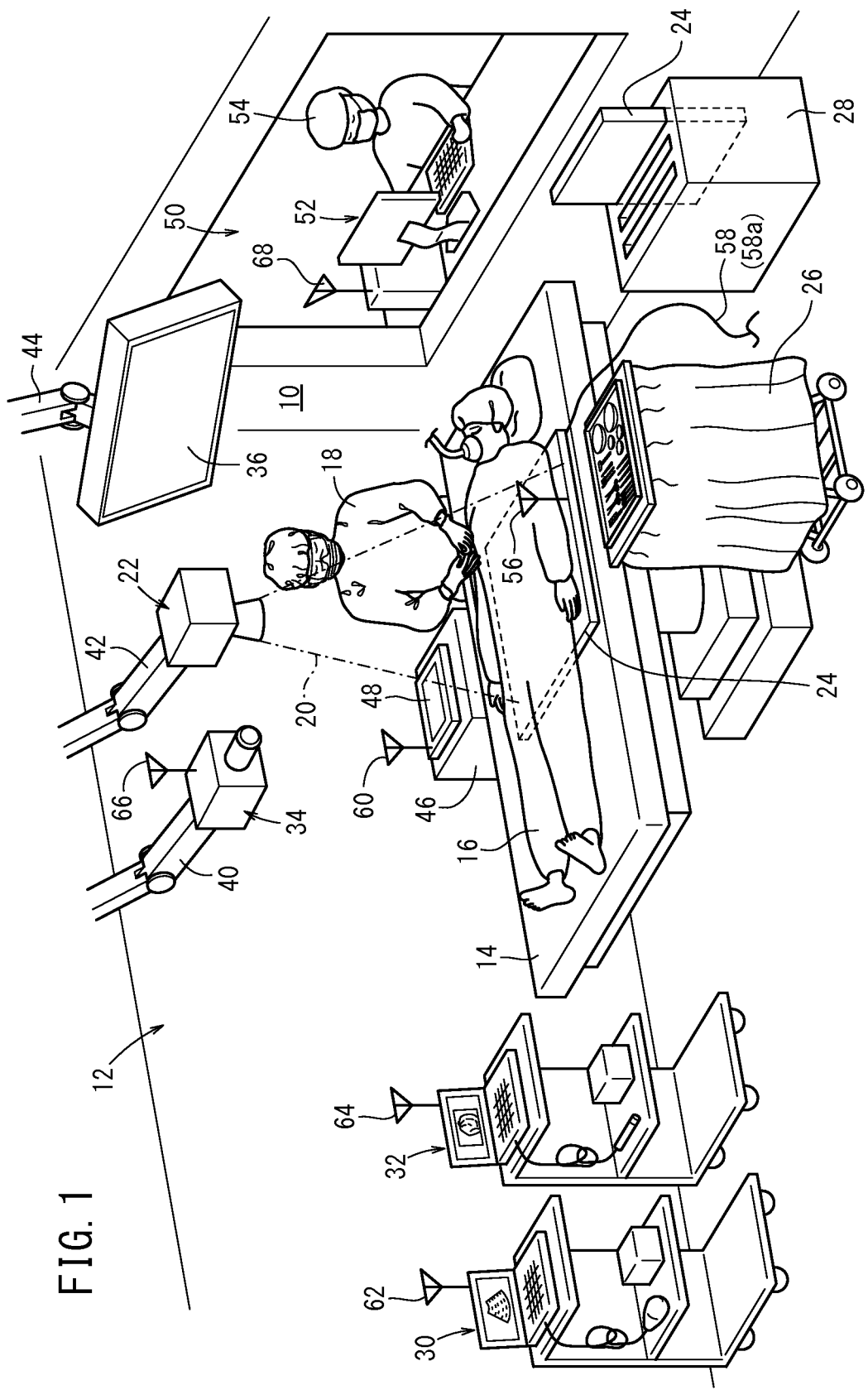
FIG. 1 is a perspective view of an operating room, in which a medical system (a radiographic image capturing system or a medical image broadcasting system) according to an embodiment of the present invention is used.

As shown in FIG. 1, for example, a medical system 10 (a radiographic image capturing system or a medical image broadcasting system) according to this embodiment is used in an operating room 12 in a medical institution. As described hereinafter, the medical system 10 of this embodiment can be used in a place other than the operating room 12. The operating room 12 will be described below by way of example.

In the operating room 12, a patient 16 (a subject or an examinee) lies on an operating table 14, and a surgeon doctor 18 conducts a procedure such as a surgical operation. A radiation output apparatus 22 for applying radiation 20 to the patient 16 is placed in the operating room 12. A radiographic image capturing apparatus 24 such as a battery-powered electronic cassette is interposed between the patient 16 and the operating table 14. The radiographic image capturing apparatus 24 is used for converting the radiation 20 transmitted through the patient 16 into a radiographic image.

The operating room 12 further contains a wagon 26 and a cradle 28. The doctor 18 put various surgical tools on the wagon 26, and the radiographic image capturing apparatus 24 is inserted into and charged in the cradle 28.

The operating room 12 is further equipped with an ultrasonic diagnosis apparatus 30 (an image capturing apparatus) for applying ultrasonic wave to a desired site in the patient 16 and for converting the wave reflected by the site into an ultrasonic image. The operating room 12 is further equipped with an endoscope apparatus 32 (an image capturing apparatus) for inserting a fiberscope into the patient 16 to capture an optical image of an internal site in the patient 16 and for performing a predetermined procedure in the internal site as necessary.

The operating room 12 is further equipped with a camera 34 (an image capturing apparatus) for capturing a moving image (camera image) of the entire operating room 12 or a part thereof, and with a large display apparatus 36 for displaying various images (such as the radiographic image, the ultrasonic image, the optical image, and the camera image).

In this embodiment, the camera 34 is connected to and supported by a multijoint arm 40 extending from the ceiling, the radiation output apparatus 22 is connected to and supported by a multijoint arm 42 extending from the ceiling, and the display apparatus 36 is connected to and supported by a multijoint arm 44 extending from the ceiling. Though one camera 34 and one display apparatus 36 are placed in the operating room 12 in FIG. 1, a plurality of the cameras 34 and the display apparatuses 36 may be placed in the operating room 12.

A table 46 is placed in the vicinity of the doctor 18 operating on the patient 16, and a mobile apparatus 48 such as a tablet computer (tablet PC), a handheld computer, or a personal digital assistant (PDA) is disposed on the table 46. The mobile apparatus 48 is a portable apparatus, which can be carried onto the table 46 disposed slightly away from the patient 16 (farther from the patient 16 than the radiographic image capturing apparatus 24) and can be manually operated by the doctor 18. In FIG. 1, a tablet PC is shown as the mobile apparatus 48 by way of example.

A console 52 is disposed as a control apparatus for controlling the radiation output apparatus 22 and the radiographic image capturing apparatus 24 in a preparation room 50 adjacent to the operating room 12. A radiologist 54 (hereinafter referred to also as the technician 54) operates the console 52 based on an instruction from the doctor 18. In this embodiment, for example, as shown in FIG. 1, the console 52 is positioned further from the patient 16 than the mobile apparatus 48. In the following description, the technician 54 includes an ultrasonic technician for operating the ultrasonic diagnosis apparatus 30 based on an instruction from the doctor 18 and an endoscope technician for operating the endoscope apparatus 32 based on an instruction from the doctor 18 in some cases.

The radiographic image capturing apparatus 24 can send signals to and receive signals from the mobile apparatus 48 via a wireless communication link using an antenna 56, and can send signals to and receive signals from the console 52 via a wired communication link using an optical fiber cable 58. The mobile apparatus 48 can send signals to and receive signals from the other apparatuses via a wireless communication link using an antenna 60. The ultrasonic diagnosis apparatus 30 can send signals to and receive signals from the mobile apparatus 48 via a wireless communication link using an antenna 62. The endoscope apparatus 32 can send signals to and receive signals from the mobile apparatus 48 via a wireless communication link using an antenna 64. The camera 34 can send signals to and receive signals from the mobile apparatus 48 via a wireless communication link using an antenna 66. The console 52 can send signals to and receive signals from the mobile apparatus 48 via a wireless communication link using an antenna 68.

In FIG. 1, the wireless communication links are formed between the apparatuses in the operating room 12. Specifically, each wireless communication link may be a near field wireless communication link such as a short-range wireless communication or a wireless PAN (Personal Area. Network), a wireless LAN (Local Area Network), etc. Alternatively, the signals may be transmitted and received via an infrared communication.

Figure 2:
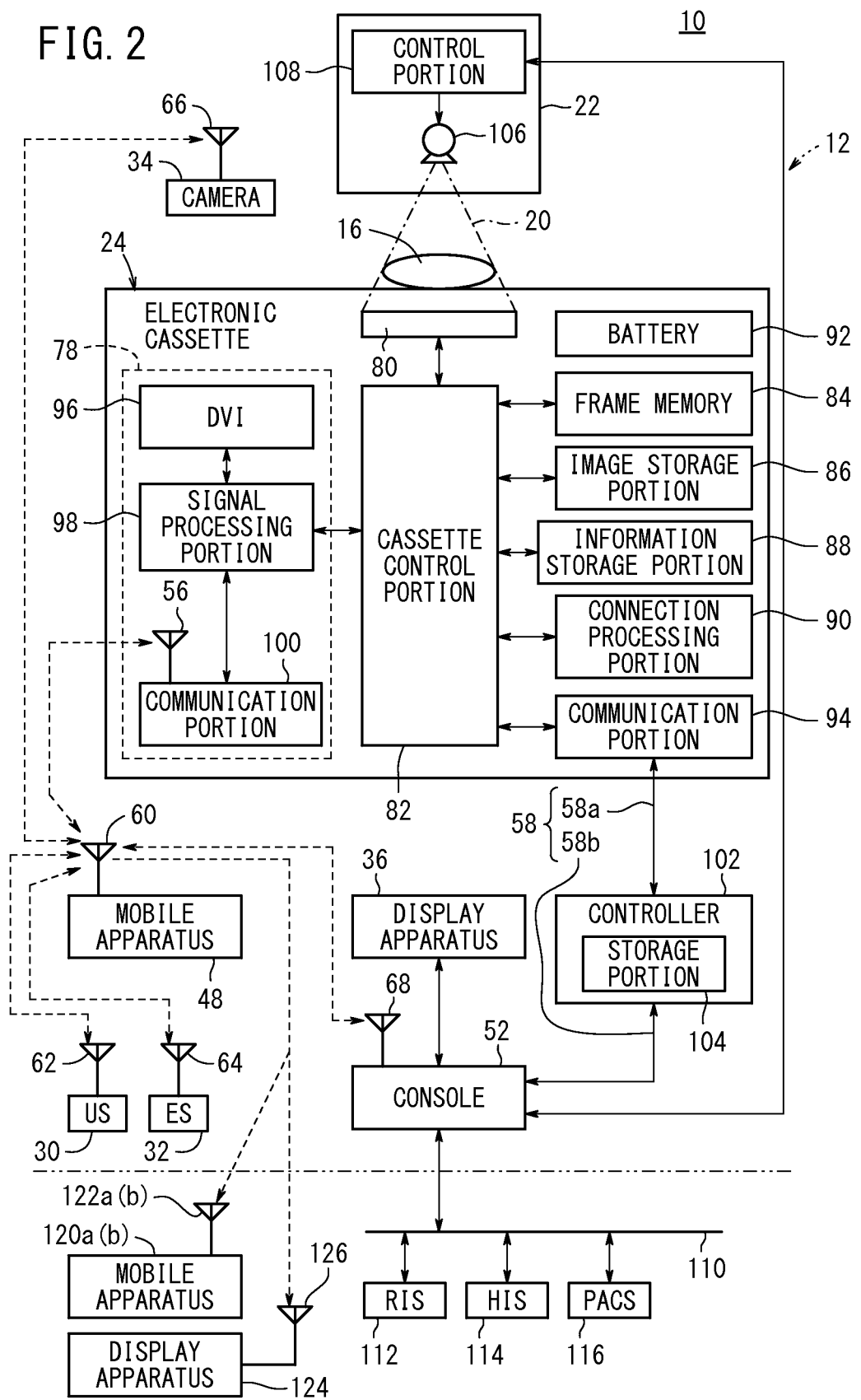
FIG. 2 is a block diagram of the medical system of FIG. 1.

As shown in FIG. 2, in the radiographic image capturing apparatus 24, the antenna 56 is contained in a backup communication portion 78, which is used as a backup of the signal transmission/reception using the optical fiber cable 58. The radiographic image capturing apparatus 24 is the battery-powered electronic cassette having the backup communication portion 78 containing the antenna 56, a radiation conversion panel 80, a cassette control portion 82, a frame memory 84, an image storage portion 86, an information storage portion 88, a connection processing portion 90, a battery 92, and a communication portion 94 (a first communication portion).

In a case where the radiation 20 is applied from the radiation output apparatus 22 to the patient 16, the radiation conversion panel 80 detects the radiation 20 transmitted through the patient 16 and converts the radiation 20 into electric signals corresponding to the radiographic image. The radiation conversion panel 80 may be a direct-conversion-type or indirect-conversion-type radiation conversion panel.

The direct-conversion-type radiation conversion panel has a radiation conversion layer containing a semiconductor such as an amorphous selenium (a-Se) for directly converting the radiation 20 into the electric signals. The indirect-conversion-type radiation conversion panel has a scintillator containing columnar CsI crystals or GOS ($Gd_2O_2S$) grains for converting the radiation 20 into fluorescence, and further has a photoelectric transducer such as a photodiode for detecting the fluorescence as the electric signals. The radiation conversion panel 80 contains a matrix of a plurality of pixels for detecting the radiation 20, and the electric signals corresponding to the radiographic image are stored temporarily as electric charges in the pixels.

In the medical system 10, the application of the radiation 20 from the radiation output apparatus 22 to the patient 16 and the conversion of the radiation 20 transmitted through the patient 16 into the radiographic image in the radiation conversion panel 80 can be repeatedly performed, whereby the radiographic images can be sequentially acquired in fluorography processes (radiographic image capturing processes). In each radiographic image capturing process (after each radiation 20 application) in the fluorography, the radiation conversion panel 80 is controlled by the cassette control portion 82, the electric charges stored in the pixels arranged in the matrix are sequentially read line by line, and the (digital) electric signals corresponding to the read electric charges are stored as a one-frame radiographic image in the frame memory 84. Thus, in the fluorography, one-frame radiographic images obtained by the image capturing processes are sequentially stored in the frame memory 84.

The information storage portion 88 stores cassette ID information for identifying the radiographic image capturing apparatus 24, order information (subject information) for requesting a fluorography of the patient 16, and image capturing conditions for applying the radiation 20 to the patient 16.

The order information is prepared by the doctor 18 in a radiology information system (RIS) 112 or a hospital information system (HIS) 114 to be hereinafter described. Specifically, the order information may include subject information for identifying the patient 16 such as the name, age, and sex of the patient 16, and may further include information of the radiation output apparatus 22 and the radiographic image capturing apparatus 24 to be used in the fluorography, the imaging area of the patient 16, the image capturing procedure, etc. The image capturing conditions may include various conditions for emitting the radiation 20 to the imaging area of the patient 16, such as the tube voltage and tube current of a radiation source 106 and the irradiation time with the radiation 20.

In the connection processing portion 90, at least the one-frame radiographic image (digital moving image data) stored in the frame memory 84 is connected to the cassette ID information, the order information, and the image capturing conditions stored in the information storage portion 88. The connected information (including the moving image, the cassette ID information, the order information, and the image capturing conditions) is stored in the image storage portion 86. Because the moving image (fluoroscopic image) has a large volume, the image storage portion 86 preferably contains an auxiliary storage device having a relatively large memory capacity such as a hard disk drive (HDD) or a memory card.

The communication portion 94 sends the connected information stored in the image storage portion 86 (including the moving image, the cassette ID information, the order information, and the image capturing conditions) to the console 52 via the optical fiber cable 58. Furthermore, the communication portion 94 receives information from the console 52 (such as the order information or the image capturing conditions) and a control signal (a command for controlling the radiographic image capturing apparatus 24) via the optical fiber cable 58.

The backup communication portion 78 contains the antenna 56, a digital visual interface (DVI) 96, a signal processing portion 98 (an image processing portion), and a communication portion 100 (a second communication portion).

The signal processing portion 98 is used for converting the moving image (digital data) stored in the image storage portion 86 into television broadcast signals (such as analog television broadcast signals). Furthermore, in the signal processing portion 98, the moving image stored in the image storage portion 86 can be subjected to a predetermined thinning (decimating) processing to obtain a thinned image. The thinned image has a smaller information amount (is formed at a lower frame rate) as compared with the moving image.

The DVI 96 is a video output interface, which is connected to a display apparatus such as a display device (not shown) and is used for outputting the television broadcast signals converted in the signal processing portion 98 (the moving image modified for analog broadcasting) on the display apparatus.

The communication portion 100 sends the television broadcast signals or the thinned image to the mobile apparatus 48 via the wireless communication link using the antenna 56. The moving image is connected to the cassette ID information, the order information, and the image capturing conditions in the image storage portion 86. Therefore, the communication portion 100 sends, to the mobile apparatus 48, the connected information (including the cassette ID information, the order information, and the image capturing conditions) in addition to the broadcast moving image or the thinned image.

The communication portion 100 is used as a backup of the communication portion 94. Therefore, in a case where there is a defect in the signal transmission/reception between the communication portion 94 and the console 52 via the optical fiber cable 58, the communication portion 100 may send the original radiographic moving image stored in the image storage portion 86 and the connected information to the mobile apparatus 48 via the wireless communication link. Alternatively, in a case where the radiographic image capturing apparatus 24 does not send the original radiographic image and the like to the outside, the original radiographic image and the various information may be temporarily stored in the image storage portion 86 and then transferred therefrom to a storage portion 104 temporarily in a controller 102 or the console 52 using an interface (not shown) such as USB (Universal Serial Bus) e.g. after the surgical operation.

The battery 92 supplies electric energy to each component in the radiographic image capturing apparatus 24.

The controller 102 is interposed between the radiographic image capturing apparatus 24 and the console 52. Thus, the optical fiber cable 58 contains an optical fiber cable 58a making a wired connection between the radiographic image capturing apparatus 24 and the controller 102, and further contains an optical fiber cable 58b making a wired connection between the controller 102 and the console 52.

The controller 102 sends the information or the command from the console 52 (such as the order information or the image capturing conditions) to the communication portion 94, and stores the connected information (including the original radiographic moving image, the cassette ID information, the order information, and the image capturing conditions) in the storage portion 104. The storage portion 104 preferably contains an auxiliary storage device such as a memory card in the same manner as the image storage portion 86. The connected information stored in the storage portion 104 is sent to the console 52 via the optical fiber cable 58b.

The radiation output apparatus 22 contains the radiation source 106 for outputting the radiation 20 and a control portion 108 for controlling the radiation source 106 based on a control signal (command) from the console 52.

The mobile apparatus 48 can receive the various information connected to the radiographic image obtained in the radiographic image capturing apparatus 24 (the original radiographic image, the thinned image, or the broadcast image). The mobile apparatus 48 can send signals to and receive signals from the console 52 via the wireless communication link.

In the case of capturing the ultrasonic image of an internal site in the patient 16, information on the patient 16 (such as the subject information or the imaging area) is registered beforehand on the ultrasonic diagnosis apparatus 30. Thus, the mobile apparatus 48 receives the ultrasonic image and such information on the patient 16 connected thereto from the ultrasonic diagnosis apparatus 30 via the wireless communication link.

In the case of capturing the optical image of an internal site in the patient 16, information on the patient 16 (such as the subject information or the imaging area) is registered beforehand on the endoscope apparatus 32. Thus, the mobile apparatus 48 receives the optical image and the patient 16 information connected thereto from the endoscope apparatus 32 via the wireless communication link.

Furthermore, the mobile apparatus 48 receives a camera image of the operating room 12 from the camera 34 via the wireless communication link.

Therefore, the mobile apparatus 48 can send to the console 52 the camera image, the ultrasonic image and the patient 16 information connected thereto, the optical image and the patient 16 information connected thereto, and the radiographic image and the various information connected thereto. Thus, the console 52 can act to display the moving images and the various connected information transmitted via the wireless communication links and the radiographic images and the various connected information transmitted via the optical fiber cable 58 on the display apparatus 36.

The console 52 is connected to the RIS 112, the HIS 114, and a medical image information system (PACS) 116 via a LAN 110 in the medical institution. The RIS 112 integrally manages radiographic images and other information handled in the radiological department of the medical institution. The HIS 114 integrally manages medical information in the hospital. The PACS 116 can receive information transmitted from the console 52 via the LAN 110 and can integrally manage the information. The information includes the moving images and the connected information obtained by the camera 34 and the medical apparatuses in the medical system 10 (such as the radiation output apparatus 22, the radiographic image capturing apparatus 24, the ultrasonic diagnosis apparatus 30, and the endoscope apparatus 32).

In this embodiment, the radiographic image capturing apparatus 24, the ultrasonic diagnosis apparatus 30, and the endoscope apparatus 32 are modality apparatuses according to DICOM (Digital Imaging and Communication in Medicine) standard. Supplementary information according to the DICOM standard and the patient 16 information to be connected are added to the generated image data (including the radiographic image, the ultrasonic image, and the optical image), and the radiographic image capturing apparatus 24, the ultrasonic diagnosis apparatus 30, and the endoscope apparatus 32 output the added data as image information. Therefore, the console 52, which is used as a DICOM server, receives the image information according to the DICOM standard from the radiographic image capturing apparatus 24, the ultrasonic diagnosis apparatus 30, and the endoscope apparatus 32, and sends the image information to the PACS 116 via the LAN 110.

The camera 34 does not meet the DICOM standard in some cases. Therefore, the moving image obtained by the camera 34 may be subjected to DICOM conversion by the console 52. The console 52 sends the converted moving image (the image information according to the DICOM standard) to the PACS 116 via the LAN 110. Because the mobile apparatus 48 and the console 52 have approximately the same structure as described hereinafter, the mobile apparatus 48 can be used as the DICOM server. The DICOM standard and the DICOM conversion are known in the art, and therefore the detailed explanations thereof are omitted in this description.

As described hereinafter, the mobile apparatus 48 can act to deliver the moving images (including the camera image, the ultrasonic image, the optical image, and the radiographic image) and the various information connected to the moving images in real time to a predetermined area in the medical institution (such as a waiting room, a meeting room, the operating room 12, or the preparation room 50) via terrestrial digital television broadcasting (or area one-segment broadcasting in Japan).

In a case where a medical expert other than the doctor 18 and the technician 54 (such as another doctor, resident, or student) has a mobile apparatus 120a such as a mobile phone or a tablet PC, a family member of the patient 16 has a mobile apparatus 120b such as a mobile phone or a tablet PC, and the mobile apparatuses 120a, 120b have antennas 122a, 122b capable of receiving the terrestrial digital television broadcasting respectively, the mobile apparatuses 120a, 120b can receive the moving images and the various information in the predetermined area. Furthermore, in a case where a display apparatus 124 capable of displaying the image delivered in real time by the terrestrial digital television broadcasting (such as a display device) is placed in the predetermined area, the display apparatus 124 can receive the moving images and the various information via an antenna 126.

Figure 3:
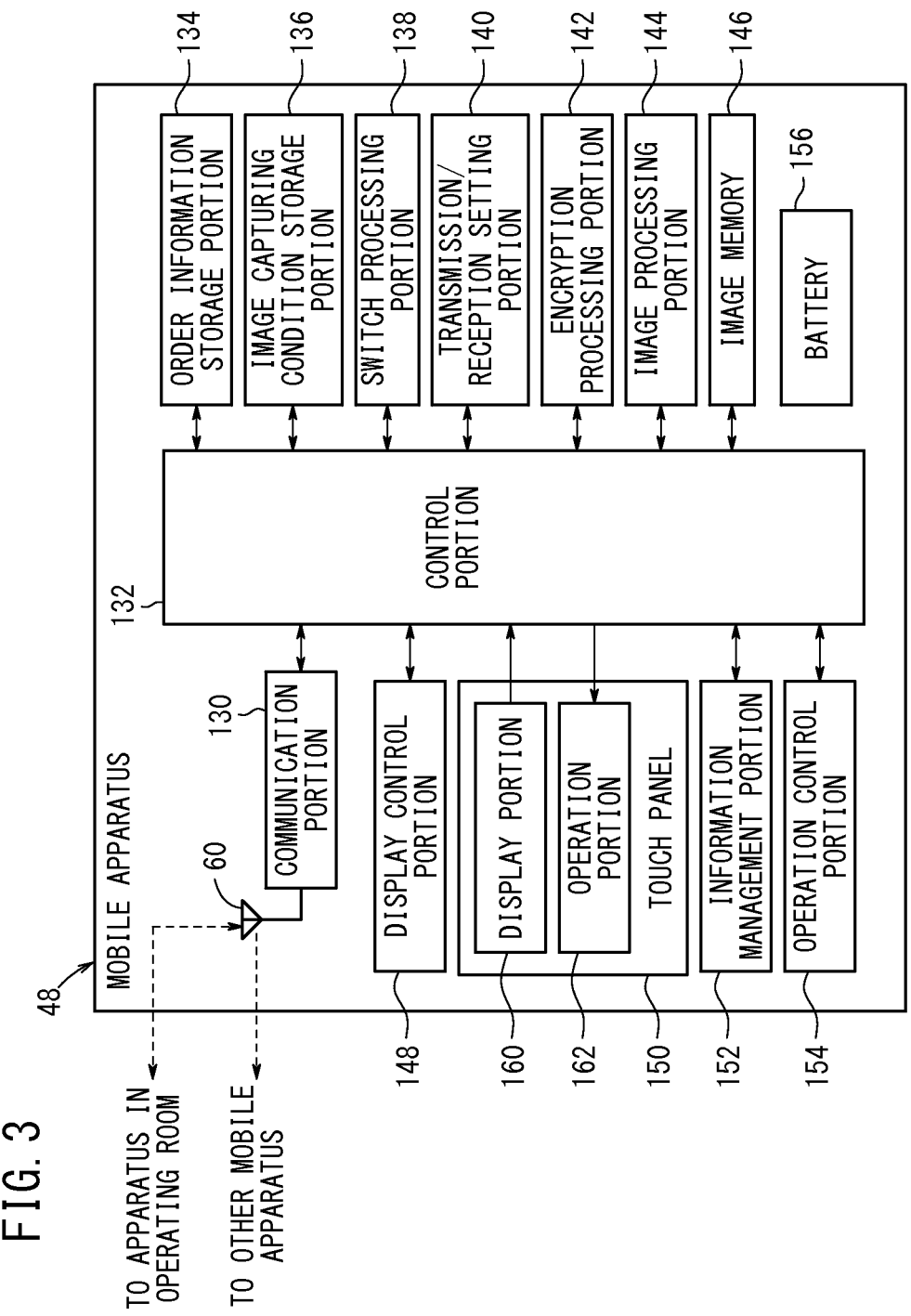
FIG. 3 is a block diagram of a mobile apparatus, which is operated by a doctor.
Figure 4:
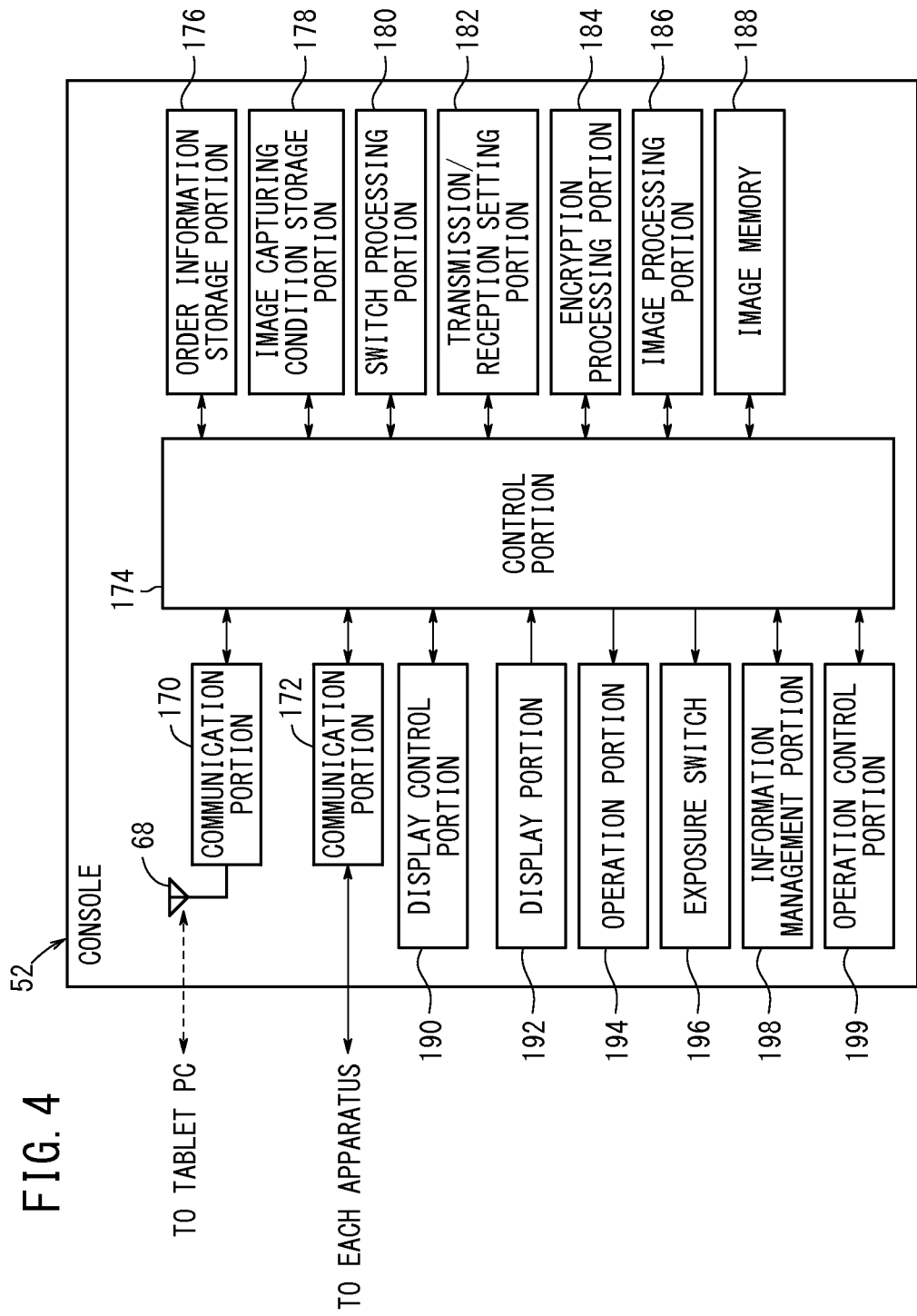
FIG. 4 is a block diagram of a console.

FIG. 3 is a block diagram of the mobile apparatus 48 operated by the doctor 18, and FIG. 4 is a block diagram of the console 52. The mobile apparatus 48 and the console 52 have approximately the same structure except for some components.

The mobile apparatus 48 has, in addition to the above antenna 60, a communication portion (image broadcasting portion) 130, a control portion 132, an order information storage portion 134, an image capturing condition storage portion 136, a switch processing portion 138, a transmission/reception setting portion 140, an encryption processing portion 142, an image processing portion 144, an image memory 146, a display control portion 148, a touch panel 150, an information management portion 152, an operation control portion 154, and a battery 156. The touch panel 150 has a display portion 160 and an operation portion 162.

The console 52 has, in addition to the above antenna 68, communication portions 170, 172, a control portion 174, an order information storage portion 176, an image capturing condition storage portion 178, a switch processing portion 180, a transmission/reception setting portion 182, an encryption processing portion 184, an image processing portion 186, an image memory 188, a display control portion 190, a display portion 192, an operation portion 194, an exposure switch 196, an information management portion 198, and an operation control portion 199.

The mobile apparatus 48 will be described below. The communication portion 130 in the mobile apparatus 48 sends signals to and receives signals from the communication portion 100 in the radiographic image capturing apparatus 24, the ultrasonic diagnosis apparatus 30, the endoscope apparatus 32, the camera 34, and the communication portion 170 in the console 52 placed in the operating room 12 via the wireless communication link using the antenna 60. Furthermore, the communication portion 130 delivers the moving images and the various connected information in real time to the predetermined area in the medical institution via the terrestrial digital television broadcasting using the antenna 60.

The control portion 132 controls the components in the mobile apparatus 48.

The order information storage portion 134 stores the order information on the patient 16, and the image capturing condition storage portion 136 stores the image capturing conditions for applying the radiation 20 to the patient 16.

The switch processing portion 138 is used for switching an apparatus (master) for controlling the radiation output apparatus 22 and the radiographic image capturing apparatus 24 between the mobile apparatus 48 and the console 52. Thus, the mobile apparatus 48 and the console 52 are a master (main apparatus) and a slave (sub apparatus) for controlling the radiation output apparatus 22 and the radiographic image capturing apparatus 24, and the switch processing portion 138 is used for switching the master and the slave between the mobile apparatus 48 and the console 52. The master sends control signals (commands) to the radiation output apparatus 22 and the radiographic image capturing apparatus 24 to directly control the apparatuses. Alternatively, the master sends the commands to the radiation output apparatus 22 and the radiographic image capturing apparatus 24 via the slave (using the slave as a transponder) to control the apparatuses.

The transmission/reception setting portion 140 presets a channel for forming a multiple wireless communication link of the communication portion 130 in the mobile apparatus 48 to the communication portion 100 in the radiographic image capturing apparatus 24, the communication portion 170 in the console 52, the camera 34, the ultrasonic diagnosis apparatus 30, and the endoscope apparatus 32 before the start of the fluorography. Furthermore, the transmission/reception setting portion 140 selects contents of the command to be sent from the mobile apparatus 48 to the radiation output apparatus 22, the radiographic image capturing apparatus 24, the ultrasonic diagnosis apparatus 30, the endoscope apparatus 32, and the camera 34. The information management portion 152 stores (manages) the preset and selected contents.

For example, the multiple communication link may utilize code division multiple access (CDMA), time division multiple access (TDMA), or frequency division multiple access (FDMA). The transmission/reception setting portion 140 preallocates the preset channel (a preset code in the CDMA system, a preset time slot in the TDMA system, or a preset frequency range in the FDMA system) to the radiation output apparatus 22 (the console 52 used as the transponder), the radiographic image capturing apparatus 24, the ultrasonic diagnosis apparatus 30, the endoscope apparatus 32, and the camera 34, and preselects the command to be sent to the apparatuses.

In a case where the communication portion 130 acts to perform the terrestrial digital television broadcasting in real time in the predetermined area, the encryption processing portion 142 is used for carrying out an encryption processing with respect to individual information or information considered as the individual information (e.g. the cassette ID information, the order information, or the image capturing conditions to be connected to the radiographic image, the patient 16 information to be connected to the ultrasonic image and the optical image, or the like), using a public key or a secret key (encryption key).

Therefore, in a case of browsing the encrypted information (decoding the various information) on the mobile apparatus 120a, 120b or the display apparatus 124 in the predetermined area, it is necessary to put (pre-register) the public key or the secret key (encryption key) into the apparatus. In the mobile apparatus 48, the information management portion 152 manages the public key or the secret key.

For example, in order that another medical expert can give an appropriate advice to the doctor 18 during the operation or provide an adequate explanation to a family member of the patient 16 while inhibiting third person's access to the individual information, the pre-registration may be performed to acquire the public key or the secret key only on the mobile apparatus 120a for the other medical expert. It is to be understood that the mobile apparatus 120b for the family of the patient 16 may be operated to acquire the encryption key.

For example, a person requiring the pre-registration (the medical expert or the family member of the patient 16) may go to a nurse center or the like in the medical institution, and may convey a request for the pre-registration to the nurse center. In the nurse center, the pre-registration processing may be performed on the mobile apparatus 120a, 120b for the person to obtain the encryption decoding key. In this case, a nurse identifies the person prior to the pre-registration. Therefore, the pre-registration of the third person not relevant to the operation of the patient 16 can be prevented.

For example, the pre-registration on the mobile apparatus 120a, 120b in the nurse center may be performed by the following processes of (1) to (3).

(1) For example, in a case where the mobile apparatus 48 is managed by the nurse center before the operation of the patient 16, the mobile apparatus 120a, 120b sends an e-mail to the mobile apparatus 48. The mobile apparatus 48 receives the e-mail and then sends a reply e-mail with the encryption decoding key to the mobile apparatus 120a, 120b. The mobile apparatus 120a, 120b receives the reply e-mail and acquire the encryption key. The encryption key is acquired in this manner, so that the mobile apparatus 120a, 120b is pre-registered on the mobile apparatus 48.

(2) Unlike the process of (1), after the mobile apparatus 48 receives the e-mail from the mobile apparatus 120a, 120b, the mobile apparatus 48 sends a reply e-mail with a two-dimensional bar code corresponding to the encryption key to the mobile apparatus 120a, 120b. The mobile apparatus 120a, 120b receives the reply e-mail and acts to display the two-dimensional bar code on the screen. The person finds the two-dimensional bar code and operates the mobile apparatus 120a, 120b to acquire the encryption decoding key corresponding to the two-dimensional bar code.

(3) Unlike the process of (2), after the mobile apparatus 48 receives the e-mail from the mobile apparatus 120a, 120b, the mobile apparatus 48 sends a reply e-mail including a URL (Uniform Resource Locator) corresponding to the encryption key to the mobile apparatus 120a, 120b. The mobile apparatus 120a, 120b receives the reply e-mail and acts to display the contents of the e-mail on the screen. The person finds the URL and operates the mobile apparatus 120a, 120b to acquire the encryption decoding key corresponding from the URL.

An MAC (Media Access Control) address may be preallocated to each apparatus to be connected to the network such as the LAN, and the medical institution may know the person requiring the pre-registration (or the mobile apparatus 120a, 120b for the person). In this case, the MAC address of the mobile apparatus 120a, 120b may be preregistered in the mobile apparatus 48, and the mobile apparatus 48 may send the encryption decoding key to the mobile apparatus 120a, 120b having the registered MAC address.

The mobile apparatus 120a, 120b may receive the encryption key from the mobile apparatus 48 without the pre-registration of the mobile apparatus 120a, 120b into the mobile apparatus 48. For example, the mobile apparatus 120a, 120b may receive (download) the encryption key from the mobile apparatus 48 via a wireless communication link or an infrared communication link. Alternatively, the encryption key may be copied into a memory card or a USB memory, and the mobile apparatus 120a, 120b may receive the encryption key from the memory card or the USB memory.

The encryption key does not have to be a constant (fixed) key. For example, the encryption key may be updated (changed) before each terrestrial digital broadcasting from the mobile apparatus 48 or before each one-frame image delivery.

In the following description, the mobile apparatus 120a for the other medical expert acquires the public key or the secret key (encryption key) (also requires the pre-registration of the mobile apparatus 120a).

In this embodiment, only the mobile apparatus 48 and the console 52 can be used for remotely controlling the radiation output apparatus 22, the radiographic image capturing apparatus 24, the ultrasonic diagnosis apparatus 30, the endoscope apparatus 32, and the camera 34 as described hereinafter. Only the doctor 18 or the technician 54 operates the mobile apparatus 48 or the console 52, and is authorized to remotely control the medical apparatuses.

Thus, the other medical expert having the mobile apparatus 120a, the family member of the patient 16 having the mobile apparatus 120b, and those viewing the images displayed on the display apparatus 124 are not authorized to control the medical apparatuses. They are authorized only to watch the moving images and the various information, delivered from the mobile apparatus 48 in real time via the terrestrial digital television broadcasting, on the mobile apparatuses 120a, 120b and the display apparatus 124.

Thus, a person other than the doctor 18 and the technician 54 cannot operate the mobile apparatus 48, the console 52, or the like to remotely control the medical apparatuses.

The image processing portion 144 conducts a predetermined image processing for displaying the moving images such as the camera image, the ultrasonic image, the optical image, and the radiographic image on the display portion 160. The processed moving images and the various information connected thereto are stored in the image memory 146. The image processing portion 144 conducts also a processing for converting the moving images stored in the image memory 146 into the terrestrial digital television broadcast signals. Furthermore, the image processing portion 144 performs the above-mentioned DICOM conversion of the camera image.

The display control portion 148 acts to display the moving images stored in the image memory 146 and the various information connected thereto on the display portion 160 of the touch panel 150. The operation portion 162 is a widget including icons and text boxes (an operation image and an exit image) displayed on the display portion 160 in the touch panel 150. In a case where the doctor 18 operates the operation portion 162, the control portion 132 performs various control processes, and the display control portion 148 controls the display portion 160 to display an image corresponding to the operation, based on the operation on operation portion by the doctor 18.

As described above, the information management portion 152 manages (stores) the contents of the channel and the command preset in the transmission/reception setting portion 140 and the public key or the secret key (encryption key) used in the encryption processing in the encryption processing portion 142.

The operation control portion 154 acts to select (limit) the widget displayed on the display portion 160, so that the doctor 18 can operate the operation portion 162 to remotely control any one of the medical apparatuses for performing the predetermined diagnosis or procedure of the patient 16: (1) the radiation output apparatus 22 and the radiographic image capturing apparatus 24, (2) the ultrasonic diagnosis apparatus 30, and (3) the endoscope apparatus 32. A large number of the medical apparatuses may be arranged closer to each other in the operating room 12. Therefore, in view of smoothly performing the surgical operation on the patient 16, it is preferred that a plurality of the medical apparatuses are not used simultaneously, and one of the medical apparatuses is used.

The battery 156 supplies electric energy to each component in the mobile apparatus 48.

The console 52 will be described below. The components having the same name in the console 52 and the mobile apparatus 48 have approximately the same function. The master and the slave can be switched between the console 52 and the mobile apparatus 48 as described above. Therefore, in the case of using the console 52 as the master, the console 52 has to have the same functions as the mobile apparatus 48 mentioned above.

The communication portion 170 sends signals to and receives signals from the communication portion 130 in the mobile apparatus 48 via the wireless communication link using the antenna 68. Furthermore, the communication portion 170 can utilize the mobile apparatus 48 as a transponder to deliver the moving images and the various connected information in real time to the predetermined area in the medical institution via the terrestrial digital television broadcasting using the antenna 68. The communication portion 172 sends signals to and receives signals from the control portion 108 in the radiation output apparatus 22, the controller 102, the communication portion 94 in the radiographic image capturing apparatus 24, and the display apparatus 36 via the wired communication link.

The control portion 174 controls the components in the console 52. The order information storage portion 176 stores the order information, and the image capturing condition storage portion 178 stores the image capturing conditions. The switch processing portion 180 is used for switching the master and the slave between the console 52 and the mobile apparatus 48.

The transmission/reception setting portion 182 presets a channel for forming a multiple wireless communication link of the console 52 to the communication portion 130 in the mobile apparatus 48 or a multiple wireless communication link of the communication portion 130 in the mobile apparatus 48 to the communication portion 100 in the radiographic image capturing apparatus 24, the communication portion 170 in the console 52, the ultrasonic diagnosis apparatus 30, the endoscope apparatus 32, and the camera 34 before the start of the fluorography. Furthermore, the transmission/reception setting portion 182 selects contents of the command to be sent from the console 52 to the radiographic image capturing apparatus 24, the radiation output apparatus 22, the ultrasonic diagnosis apparatus 30, the endoscope apparatus 32, and the camera 34. The information management portion 198 stores (manages) the preset and selected contents.

In a case where the communication portion 170 acts to perform the terrestrial digital television broadcasting via the mobile apparatus 48 in real time in the predetermined area, the encryption processing portion 184 is used for subjecting the individual information of the patient 16 to the encryption processing using the public key or the secret key (encryption key). The information management portion 198 stores the public key or the secret key.

The image processing portion 186 conducts a predetermined image processing for displaying the moving images such as the camera image, the ultrasonic image, the optical image, and the radiographic image on the display portion 192. Furthermore, the image processing portion 186 performs the DICOM conversion of the camera image. The processed moving images and the various information connected thereto are stored in the image memory 188. In addition, the image processing portion 186 conducts also a processing for converting the moving images stored in the image memory 188 into the terrestrial digital television broadcast signals.

The display control portion 190 acts to display the moving images stored in the image memory 188 and the various information connected thereto on the display portion 192. In this case, the display control portion 190 can act to display the same contents on the display portion 192 as those on the display portion 160 of the touch panel 150.

The operation portion 194 in the console 52 is a keyboard or a mouse. The doctor 18 or the technician 54 operates the keyboard or the mouse (the operation portion 194) while watching the contents displayed on the display portion 192. The control portion 174 performs various control processes in response to the operation in the operation portion 194 by the doctor 18 or the technician 54. The display control portion 190 controls the display portion 192 to display an image corresponding to the operation in the operation portion 194 by the doctor 18 or the technician 54.

As described above, the information management portion 198 manages (stores) the contents of the channel and the command preset in the transmission/reception setting portion 182 and the public key or the secret key (encryption key) used in the encryption processing in the encryption processing portion 184.

The operation control portion 199 acts to select (limit) the widget displayed on the display portion 192, so that the doctor 18 or the technician 54 can operate the operation portion 194 to remotely control any one of the medical apparatuses for performing the predetermined diagnosis or procedure of the patient 16: (1) the radiation output apparatus 22 and the radiographic image capturing apparatus 24, (2) the ultrasonic diagnosis apparatus 30, and (3) the endoscope apparatus 32.

The exposure switch 196 is an exposure button for starting the emission of the radiation 20. In a case where the doctor 18 or the technician 54 operates the exposure switch 196, the control portion 174 generates a synchronization control signal for synchronizing the start of the radiation 20 output from the radiation source 106 with the detection of the radiation 20 and the conversion to the radiographic image in the radiation conversion panel 80, thereby performing the fluorography in the imaging area of the patient 16. Thus, the console 52 sends a command corresponding to the synchronization control signal to the control portion 108, and further sends the command to the radiographic image capturing apparatus 24 via the controller 102.

Figure 5:
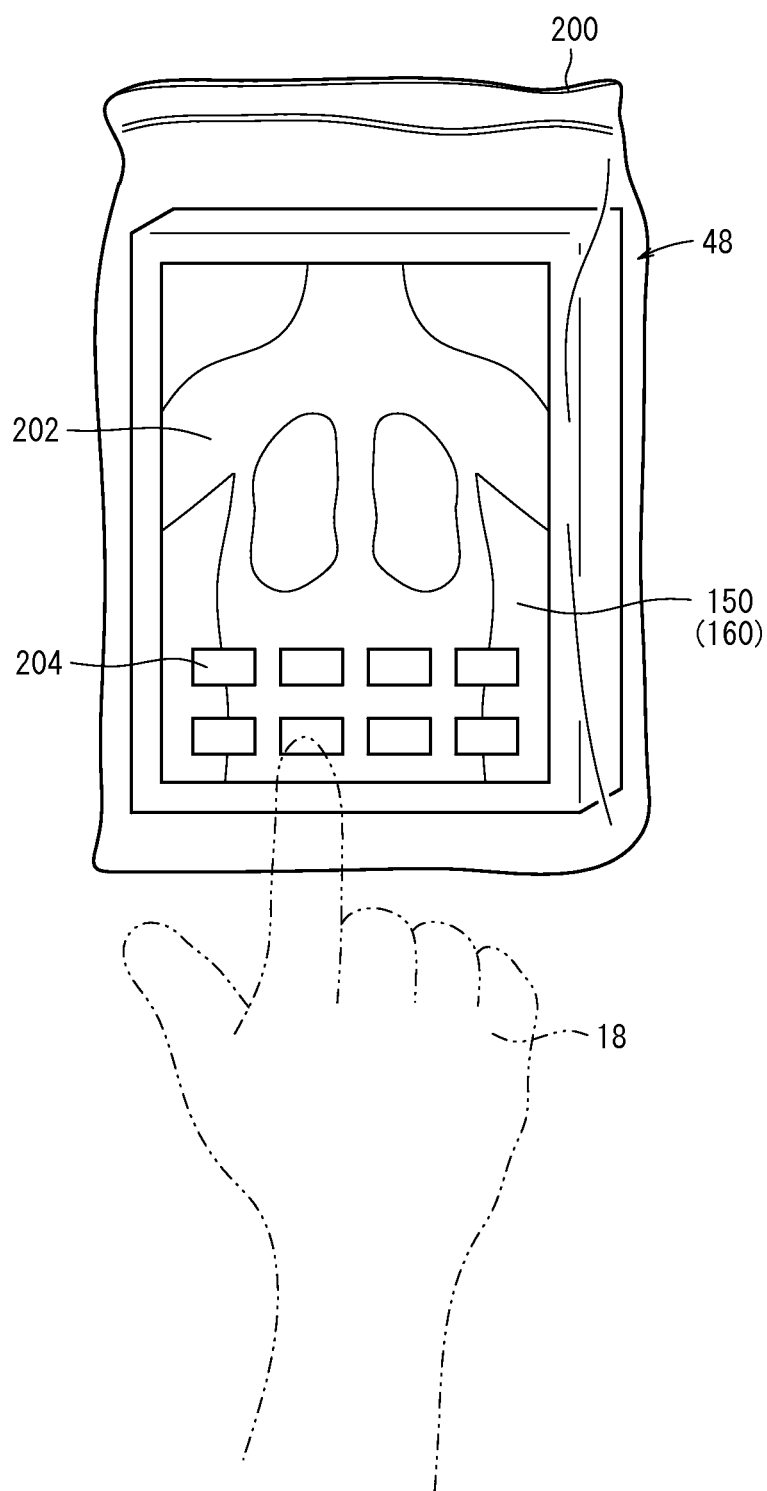
FIG. 5 is a perspective view of the mobile apparatus sealed in a sterilized bag, which is operated by the doctor.

FIG. 5 is a view of the tablet PC used as the mobile apparatus 48 operated by the doctor 18.

The mobile apparatus 48 is sealed in a sterilized bag 200 and operated in this state. In FIG. 5, a moving image 202 of the patient 16 (the radiographic image) and operation icons 204 for the doctor 18 are displayed on the display portion 160 in the touch panel 150.

Specific Function of Embodiment

Specific functions (first to third specific functions) of the medical system 10 having the above structure according to this embodiment will be described below with reference to FIGS. 6A to 10B.

The first specific function is to switch the mobile apparatus 48 from the slave to the master and the console 52 from the master to the slave after the start of the fluorography, whereby procedures such as change of the image capturing conditions and positioning of the patient 16 can be rapidly and appropriately performed after the start of the fluorography.

The second specific function is to use the mobile apparatus 48 as a remote controller in hand for controlling the various medical apparatuses, whereby the doctor 18 in the operating room 12 can remotely operate the medical apparatuses.

The third specific function is to deliver the moving images and the like of the patient 16 in the operating room 12 in real time via the terrestrial digital television broadcasting to the family member of the patient 16 and the medical expert (the mobile apparatuses 120a, 120b and the display apparatus 124) in the predetermined area.

The first to third specific functions will be described in detail below.

[First Specific Function]

Concerning the first specific function, until the start of the fluorography, the switch processing portion 180 in the console 52 (see FIG. 4) acts to maintain the console 52 as the master for controlling the radiation output apparatus 22 and the radiographic image capturing apparatus 24 (see FIGS. 1 and 2) and to maintain the mobile apparatus 48 as the slave. In a case where the doctor 18 verbally instructs the technician 54 to start the fluorography on the patient 16 during the surgical operation, the technician 54 has to operate the console 52 to perform procedures including the setting of the image capturing conditions. Therefore, it is necessary to maintain the console 52 as the master until the start of the fluorography.

As described above, the mobile apparatus 48 and the console 52 can send signals to and receive signals from each other via the wireless communication link. Therefore, the switch processing portion 180 can send the relationship between the master and the slave from the communication portion 170 to the switch processing portion 138 in the mobile apparatus 48 (see FIG. 3) via the wireless communication link before the start of the fluorography. Consequently, the mobile apparatus 48 can recognize that the mobile apparatus 48 is the slave before the start of the fluorography. The control portion 132 controls the components in the mobile apparatus 48 based on the sent information such that the mobile apparatus 48 does not act as the master (the mobile apparatus 48 does not act to control the radiation output apparatus 22 and the radiographic image capturing apparatus 24 in response to the operation on the touch panel 150 by the doctor 18).

After the preparation for the fluorography is completed, in a case where the technician 54 operates the exposure switch 196, the control portion 174 generates the synchronization control signal in response to the operation, and the communication portion 172 sends the synchronization control signal (command) to the radiation output apparatus 22 and the radiographic image capturing apparatus 24, the switch processing portion 180 judges that the fluorography is started. Then, the switch processing portion 180 acts to switch the console 52 to the slave and to switch the mobile apparatus 48 to the master based on the judgment.

The switch processing portion 180 acts to send information on the master switching from the communication portion 170 to the switch processing portion 138 in the mobile apparatus 48 via the wireless communication link. Then, the mobile apparatus 48 recognizes that the mobile apparatus 48 is switched to the master after the start of the fluorography, and the control portion 132 controls the components in the mobile apparatus 48 based on the information to utilize the mobile apparatus 48 as the master. Consequently, the doctor 18 can operate the mobile apparatus 48 in hand to control the radiation output apparatus 22 and the radiographic image capturing apparatus 24.

The console 52 is switched to the slave, and the control portion 174 controls the components in the console 52 to prevent the console 52 from acting as the master (from controlling the radiation output apparatus 22 and the radiographic image capturing apparatus 24 in response to the operation on the operation portion 194 by the technician 54).

Figure 6A:
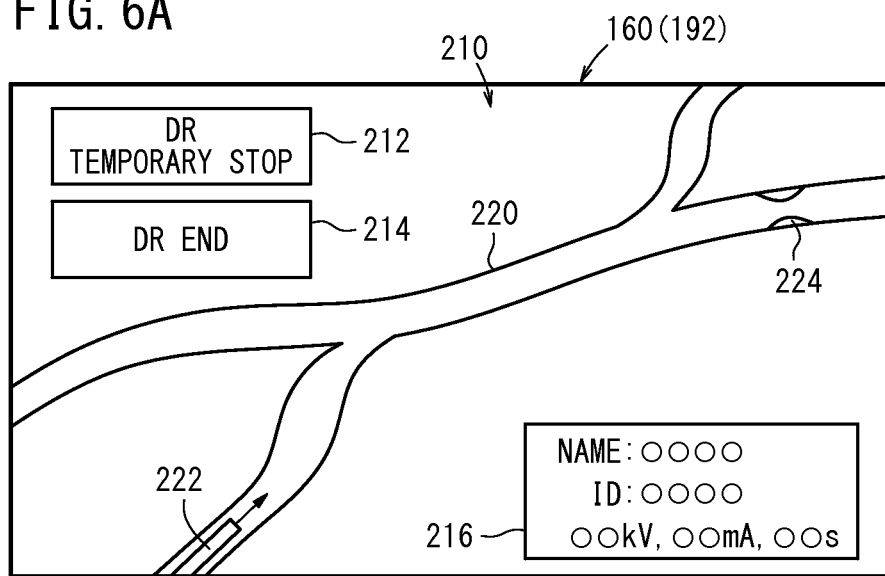
FIGS. 6A and 6B are explanatory views for illustrating a first specific function.

FIG. 6A is a view of contents displayed on the display portion 160 of the touch panel 150 in the fluorography.

A moving image 210 of the patient 16 is displayed on the screen of the display portion 160, two icons 212, 214 are further displayed thereon, and an individual information display area 216 including the name, ID, and image capturing conditions of the patient 16 is further displayed thereon. The icon 212 is an operation icon for temporarily stopping (interrupting) the fluorography, and the icon 214 is an operation icon (end icon) for ending the fluorography. For example, the moving image 210 is a radiographic image of a catheter 222 inserted into a blood vessel 220 in the patient 16. The catheter 222 is moved in the blood vessel 220 toward a narrowed portion 224.

The display control portion 148 (see FIG. 3) preferably acts to prevent the icons 212, 214 and the individual information display area 216 from overlapping with the blood vessel 220, the catheter 222, and the narrowed portion 224. The positions of such icons and individual information display area are appropriately changed depending on the contents of the moving image on the screen of the display portion 160 in FIG. 6A, as well as in FIGS. 6B to 10B.

In a case where the desired image is acquired in the fluorography, the doctor 18 may operate (touch) the icon 214 to end the fluorography. In response to the operation of the icon 214 by the doctor 18, the control portion 132 acts to send a command instructing to end the fluorography from the communication portion 130 to the radiographic image capturing apparatus 24 (see FIGS. 1 and 2) via the wireless communication link, and further acts to send the command from the console 52 to the radiation output apparatus 22. Consequently, the control portion 108 receives the command and acts to stop the radiation 20 output from the radiation source 106 based on the command.

In a case where the doctor 18 operates the icon 214 or sends the command, the switch processing portion 138 judges that the fluorography is ended. The switch processing portion 138 acts to switch the mobile apparatus 48 to the slave and to switch the console 52 to the master based on the judgment. Furthermore, the switch processing portion 138 acts to send information on the master switching from the communication portion 130 to the switch processing portion 180 in the console 52 (see FIG. 4) via the wireless communication link.

Consequently, the console 52 can recognize that the fluorography is ended and the console 52 is switched to the master. The technician 54 can operate the console 52 to control the radiation output apparatus 22 and the radiographic image capturing apparatus 24. The mobile apparatus 48 is switched to the slave, and the control portion 132 controls the components in the mobile apparatus 48 to prevent the mobile apparatus 48 from acting as the master.

In a case where the radiographic image displayed on the display portion 160 is not clear to the doctor in the fluorography (e.g. because of the low contrast of the image or the body motion of the patient 16), the doctor 18 decides to temporarily stop (interrupt) the fluorography and operates (touches) the icon 212 for temporarily stopping the fluorography, so that the image capturing conditions are reset and the patient 16 is correctly positioned.

Then, the control portion 132 acts to send a command instructing to temporarily stop the emission of the radiation 20 from the communication portion 130 to the radiographic image capturing apparatus 24 via the wireless communication link, and further acts to send the command from the console 52 to the radiation output apparatus 22. Consequently, the control portion 108 receives the command and acts to interrupt the output of the radiation 20 from the radiation source 106 based on the command. Meanwhile, the mobile apparatus 48 is maintained as the master by the switch processing portion 138 during the interruption of the fluorography.

Figure 6B:
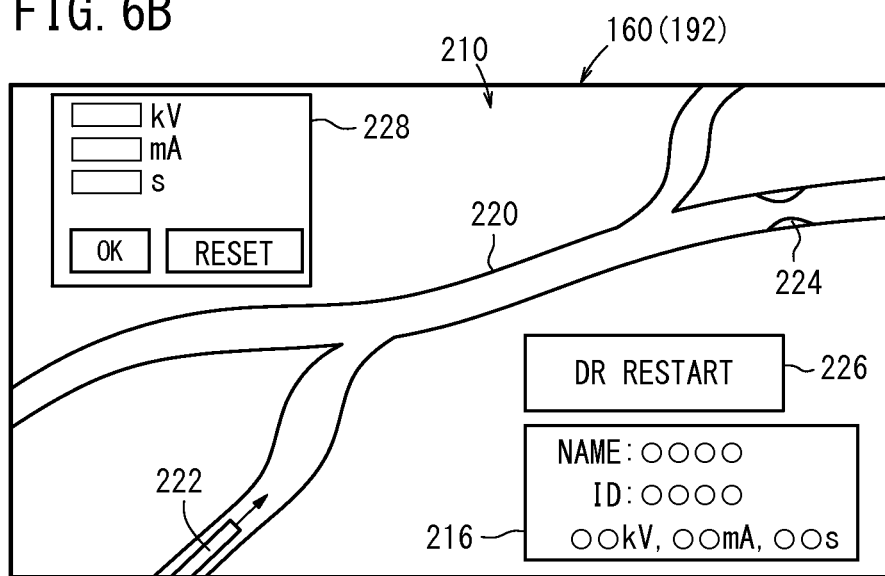

FIG. 6B is a view of contents displayed on the display portion 160 during the interruption of the fluorography.

In this case, the moving image 210 is displayed on the screen of the display portion 160, and the individual information display area 216, an icon 226, and a text box display area 228 are further displayed thereon. The icon 226 is an operation icon for restarting the interrupted fluorography.

The text box display area 228 is a widget for changing the image capturing conditions in the fluorography. Thus, the text box display area 228 contains text boxes for changing the image capturing conditions (including the tube voltage and current of the radiation source 106 and the irradiation time of the radiation 20), an OK button for determining the change in the text box, and a RESET button for resetting or canceling the change.

The doctor 18 may input desired conditions in the text boxes and push the OK button to change the image capturing conditions. The image capturing conditions changed by the doctor 18 are stored in the image capturing condition storage portion 136. The display control portion 148 controls the display portion 160 to switch the image capturing conditions displayed in the individual information display area 216 to the changed conditions. In a case where the technician 54 performs the positioning of the patient 16, the image capturing conditions are not changed in the text box display area 228.

In a case where the doctor 18 operates the icon 226, the control portion 132 acts to send a command instructing to restart the radiation 20 emission (under the changed image capturing conditions) from the communication portion 130 to the radiographic image capturing apparatus 24 via the wireless communication link, and further acts to send the command from the console 52 to the radiation output apparatus 22. Consequently, the control portion 108 receives the command and acts to restart the radiation 20 output from the radiation source 106 based on the command (under the changed image capturing conditions).

Though the master and the slave are switched by the switch processing portion 138, 180 in the master (the mobile apparatus 48 or the console 52) in the above description, the signals can be transmitted between the mobile apparatus 48 and the console 52 via the wireless communication link, and the master and the slave can be switched by the switch processing portion 138, 180 in the slave.

The displayed contents shown in FIGS. 6A and 6B may be sent from the mobile apparatus 48 to the console 52 via the wireless communication link. In a case where the doctor 18 operates the mobile apparatus 48 to change the image capturing conditions, the changed image capturing conditions may be sent from the mobile apparatus 48 to the console 52 via the wireless communication link. As a result, the same contents can be displayed on the display portion 160 in the touch panel 150 and the display portion 192 in the console 52, and the changed image capturing conditions can be stored also in the image capturing condition storage portion 178.

[Second Specific Function]

Concerning the second specific function, the doctor 18 operates the mobile apparatus 48 in hand to remotely control the medical apparatuses such as the radiation output apparatus 22, the radiographic image capturing apparatus 24, the ultrasonic diagnosis apparatus 30, and the endoscope apparatus 32 in a predetermined diagnosis or procedure on the patient 16. The medical apparatuses are less sterilized as compared with the surgical tools for the doctor 18 (and thereby cannot be directly operated by the doctor 18).

In this case, before the medical apparatuses are controlled by the mobile apparatus 48, e.g. before the fluorography is started, the transmission/reception setting portion 140 in the mobile apparatus 48 sets a channel in the medical apparatuses, the camera 34, and the console 52, and selects a command to be sent from the mobile apparatus 48 to the apparatuses, so that a multiple wireless communication link can be formed between the communication portion 130 and the apparatuses. The information management portion 152 manages the contents of the channel and command.

FIGS. 7A to 9B are views of contents displayed on the display portion 160 in a case where the doctor 18 (see FIGS. 1 and 5) operates the touch panel 150 in the mobile apparatus 48 to control the medical apparatuses in the diagnosis or procedure on the patient 16. The display control portion 148 acts to display the contents on the display portion 160 based on instructions (information) from the operation control portion 154 (see FIG. 3).

Figure 7A:
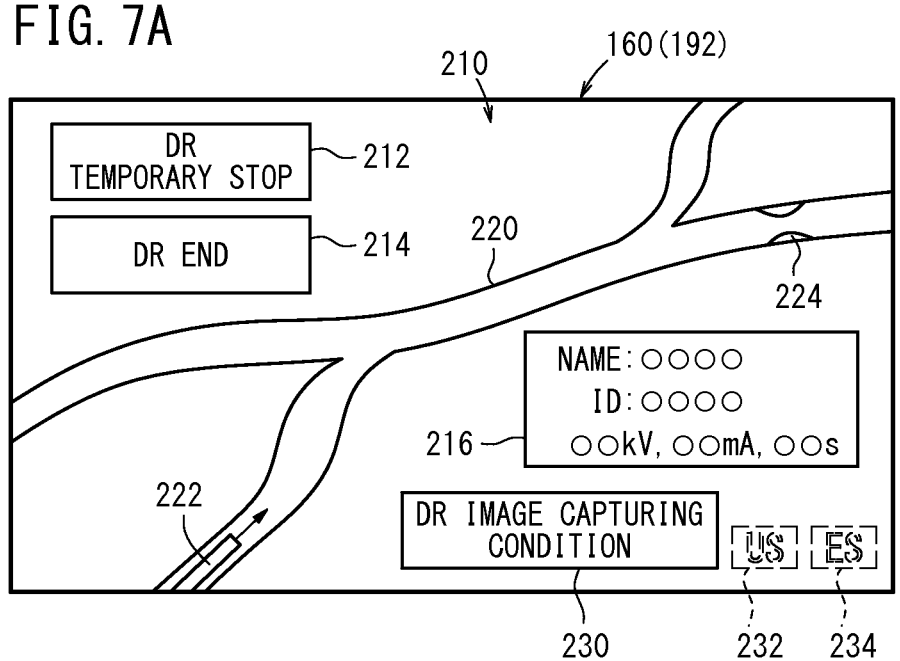
FIGS. 7A and 7B are explanatory views for illustrating a second specific function.

FIG. 7A is a view of contents displayed on the display portion 160 in the touch panel 150 in the case of controlling the radiation output apparatus 22 and the radiographic image capturing apparatus 24 (see FIGS. 1 and 2) to acquire the radiographic image of the patient 16.

The moving image 210, the icons 212, 214, and the individual information display area 216 are displayed on the screen of the display portion 160, and three icons 230, 232, 234 are further displayed thereon. The icon 230 is an operation icon for changing the image capturing conditions in the fluorography. The icon 232 is a selection icon, which the doctor 18 selects to control the ultrasonic diagnosis apparatus 30. The icon 234 is a selection icon, which the doctor 18 selects to control the endoscope apparatus 32.

In FIG. 7A, for the purpose of controlling the radiation output apparatus 22 and the radiographic image capturing apparatus 24 to acquire the radiographic image of the patient 16, the contents of the fluorography are displayed on the screen of the display portion 160, while the icon 232 for selecting the ultrasonic diagnosis apparatus 30 and the icon 234 for selecting the endoscope apparatus 32 are shown by broken lines and cannot be selected.

The diagnosis or procedure currently on the patient 16 is the acquisition of the radiographic image of the patient 16. Therefore, the operation control portion 154 informs the display control portion 148 that only the icons 212, 214, 230 can be operated in FIG. 7A, and the display control portion 148 acts based on the information to show the icons 232, 234 using the broken lines on the screen of the display portion 160.

The icons 212, 214, 230, associated with the control subjects (operation subjects) of the radiation output apparatus 22 and the radiographic image capturing apparatus 24, are displayed larger than the non-selectable icons 232, 234.

Thus, in the case of using one of a large number of the medical apparatuses placed in the operating room 12, the one medical apparatus is made operable, and the other medical apparatuses are made inoperable. Therefore, the doctor 18 can remotely control the operation subject of the one medical apparatus reliably, and can smoothly operate on the patient 16.

In FIG. 7A, in a case where the doctor 18 operates the icon 230, the operation control portion 154 judges the operation on the icon 230 by the doctor 18 to be valid and sends information on the judgment to the display control portion 148. The display control portion 148 acts based on the information to display the contents of FIG. 6B on the display portion 160. Consequently, the doctor 18 can change the image capturing conditions and can operate the mobile apparatus 48 to control the radiation output apparatus 22 and the radiographic image capturing apparatus 24.

To change the image capturing conditions, it is necessary to interrupt the fluorography. Therefore, in a case where the icon 212 for temporarily stopping the fluorography is not operated and the icon 230 is operated, the operation control portion 154 sends the information on the judgment to the control portion 132, and the control portion 132 acts to send a command instructing to interrupt the fluorography from the communication portion 130 to the radiographic image capturing apparatus 24 and the console 52 (and thus the radiation output apparatus 22) based on the information.

In FIG. 7A, in a case where the doctor 18 operates the icon 232, 234 by mistake, the operation control portion 154 judges the operation by the doctor 18 to be invalid and sends information on the judgment to the display control portion 148. The display control portion 148 acts based on the information to maintain the displayed contents shown in FIG. 7A.

In a case where the doctor 18 operates the icon 214, the operation control portion 154 judges that the operation on the icon 214 by the doctor 18 is valid as instructing to end the fluorography. The operation control portion 154 sends information on the judgment to the display control portion 148 and the control portion 132.

The control portion 132 sends a command instructing to end the fluorography from the communication portion 130 to the radiographic image capturing apparatus 24 and the console 52 (and thus the radiation output apparatus 22) based on the information, and thereby acts to end the fluorography.

Figure 7B:
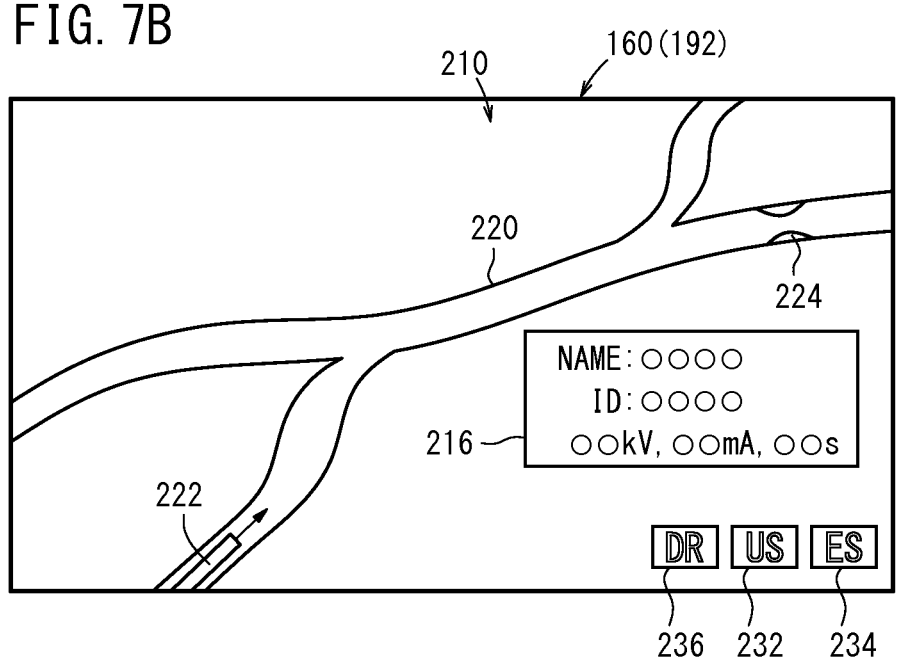

The display control portion 148 switches the contents displayed on the display portion 160 from FIG. 7A to FIG. 7B based on the information. In FIG. 7B, the moving image 210, the individual information display area 216, and three icons 232 to 236 are displayed on the display portion 160. In this case, lines representing the two icons 232, 234 are switched from the broken lines to solid lines. The icon 236 is a selection icon, which the doctor 18 selects to control the radiation output apparatus 22 and the radiographic image capturing apparatus 24.

After the fluorography is ended, all the medical apparatuses in the operating room 12 are temporarily in the unused states. Therefore, the selectable icons 232 to 236 corresponding to all the medical apparatuses are selectably displayed on the display portion 160. Thus, in a case where the doctor 18 operates the icon 232, the doctor 18 can control the ultrasonic diagnosis apparatus 30. In a case where the doctor 18 operates the icon 234, the doctor 18 can control the endoscope apparatus 32. In a case where the doctor 18 operates the icon 236, the doctor 18 can control the radiation output apparatus 22 and the radiographic image capturing apparatus 24.

Specifically, in a case where one of the three icons 232 to 236 is operated, the operation control portion 154 judges that the operation on the icon is valid and that the medical apparatus corresponding to the icon is to be controlled next. The operation control portion 154 sends information on the judgment to the control portion 132 and the display control portion 148. Based on the information, the control portion 132 informs the medical apparatus via the communication portion 130 that the medical apparatus is to be controlled by the mobile apparatus 48. Furthermore, the display control portion 148 switches the contents on the display portion 160 to those corresponding to the selected medical apparatus based on the information.

Figure 8A:
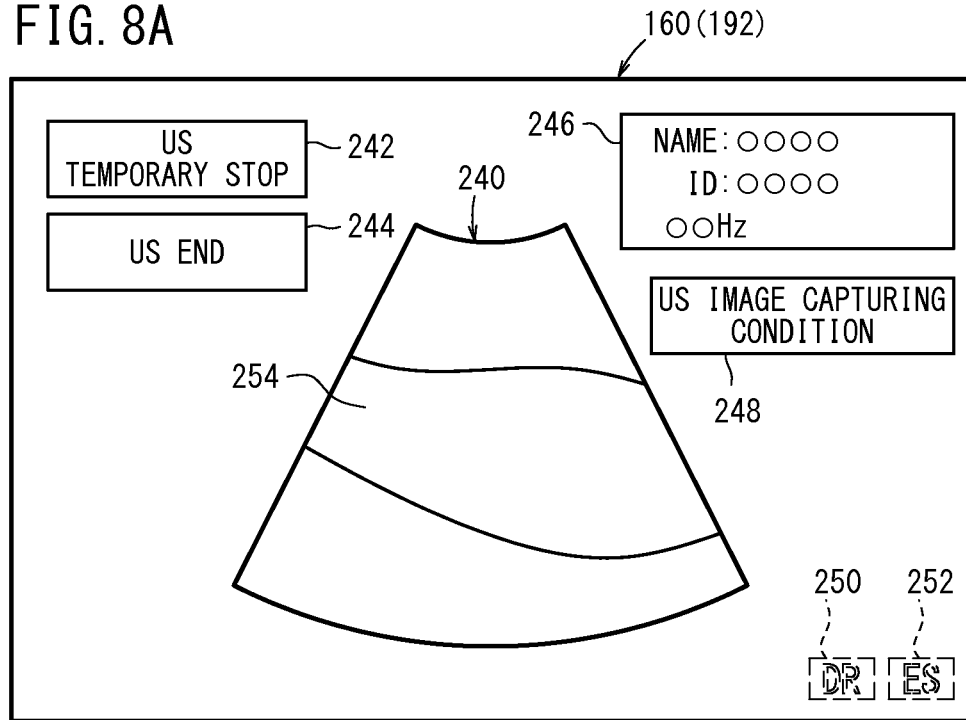
FIGS. 8A and 8B are explanatory views for illustrating the second specific function.

FIG. 8A is a view of contents displayed on the display portion 160 in the touch panel 150 in a case where the ultrasonic diagnosis apparatus 30 is controlled to acquire the ultrasonic image of the patient 16.

An ultrasonic moving image 240, icons 242, 244, and 248 to 252, and an individual information display area 246 are displayed on the screen of the display portion 160. The moving image 240 contains an organ 254 of the patient 16.

Figure 8B:
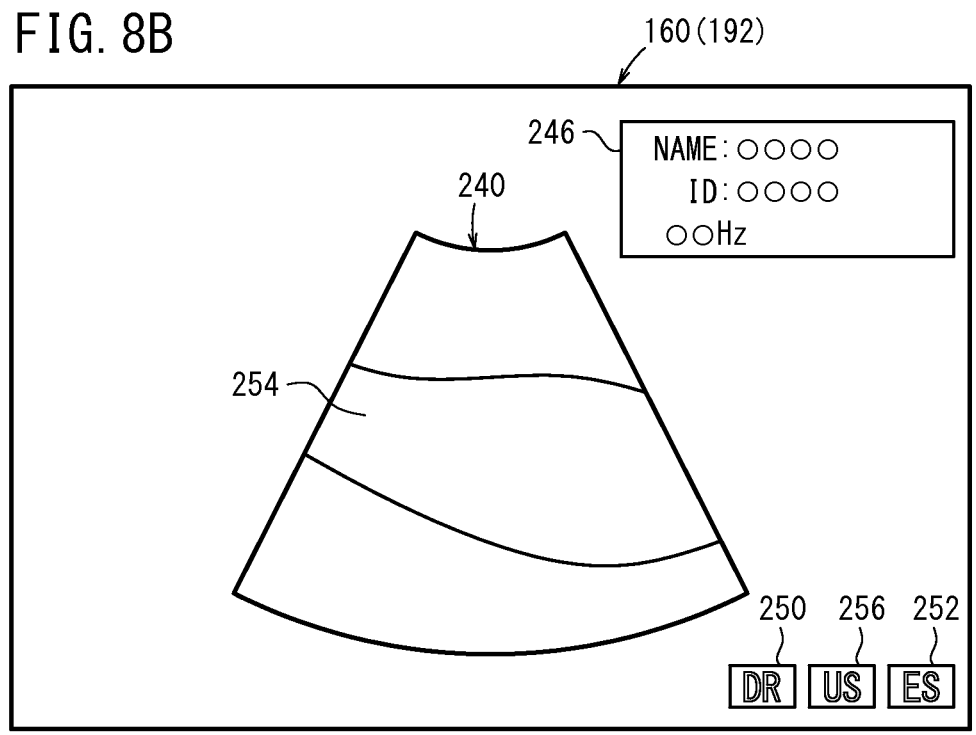

The icon 242 is an operation icon for temporarily stopping (interrupting) the ultrasonic moving image capturing, and the icon 244 is an operation icon for ending the moving image capturing. The individual information display area 246 includes the name and ID of the patient 16, the maximum depth, sound output, and ultrasonic frequency of the ultrasonic diagnosis apparatus 30, and the ultrasonic image display mode changed by controlling ultrasonic pulse (such as a normal B mode, a tissue harmonic imaging B mode, or a color Doppler mode). In FIGS. 8A and 8B, the name and ID of the patient 16 and the ultrasonic frequency are displayed in the individual information display area 246 by way of example.

The icon 248 is an operation icon for changing the image capturing conditions (such as the ultrasonic frequency) in the image capturing. The icon 250 is a selection icon, which the doctor 18 selects to control the radiation output apparatus 22 and the radiographic image capturing apparatus 24. The icon 252 is a selection icon, which the doctor 18 selects to control the endoscope apparatus 32.

In FIG. 8A, for the purpose of controlling the ultrasonic diagnosis apparatus 30 to acquire the ultrasonic image of the patient 16, the contents of the ultrasonic image capturing are displayed on the screen of the display portion 160, while the icons 250, 252 are shown by broken lines and cannot be selected.

The diagnosis or procedure on the patient 16 is the acquisition of the ultrasonic image of the patient 16. Therefore, the operation control portion 154 informs the display control portion 148 that only the icons 242, 244, 248 can be operated in FIG. 8A, and the display control portion 148 acts based on the information to show the icons 250, 252 using the broken lines on the screen of the display portion 160.

The icons 242, 244, 248, associated with the operation subjects of the ultrasonic diagnosis apparatus 30, are displayed larger than the non-selectable icons 250, 252.

In a case where the doctor 18 operates the icon 248, the operation control portion 154 judges the operation on the icon 248 to be valid and sends information on the judgment to the display control portion 148. The display control portion 148 acts based on the information to display the contents for changing the image capturing conditions of the ultrasonic diagnosis apparatus 30 on the display portion 160. Consequently, the doctor 18 can change the image capturing conditions and can operate the mobile apparatus 48 to control the ultrasonic diagnosis apparatus 30.

Also in this case, to change the image capturing conditions, it is necessary to interrupt the moving image capturing. Therefore, in a case where the icon 242 for temporarily stopping the moving image capturing is not operated and the icon 248 is operated, the operation control portion 154 sends the information on the judgment to the control portion 132, and the control portion 132 acts to send a command instructing to interrupt the moving image capturing from the communication portion 130 to the ultrasonic diagnosis apparatus 30. In FIG. 8A, in a case where the doctor 18 operates the icon 250, 252 by mistake, the operation control portion 154 judges the operation by the doctor 18 to be invalid and sends information on the judgment to the display control portion 148.

In a case where the doctor 18 operates the icon 244, the operation control portion 154 judges that the operation on the icon 244 by the doctor 18 is valid as instructing to end the moving image capturing. The operation control portion 154 sends information on the judgment to the display control portion 148 and the control portion 132. The control portion 132 sends a command instructing to end the moving image capturing from the communication portion 130 to the ultrasonic diagnosis apparatus 30 based on the information, and thereby acts to end the moving image capturing.

The display control portion 148 switches the contents displayed on the display portion 160 from FIG. 8A to FIG. 8B based on the information. In FIG. 8B, the moving image 240, the individual information display area 246, and three icons 250, 252, 256 are displayed on the display portion 160. In this case, lines representing the two icons 250, 252 are switched from the broken lines to solid lines. The icon 256 is a selection icon, which the doctor 18 selects to control the ultrasonic diagnosis apparatus 30.

Also in this case, after the moving image capturing is ended, all the medical apparatuses in the operating room 12 are temporarily in the unused states. Therefore, the selectable icons 250, 252, 256 corresponding to all the medical apparatuses are displayed on the display portion 160. In a case where the doctor 18 operates one of the icons, the operation control portion 154 acts to control the control portion 132 and the display control portion 148, so that the medical apparatus corresponding to the operated icon can be controlled and the contents corresponding to the medical apparatus can be displayed on the display portion 160.

Figure 9A:
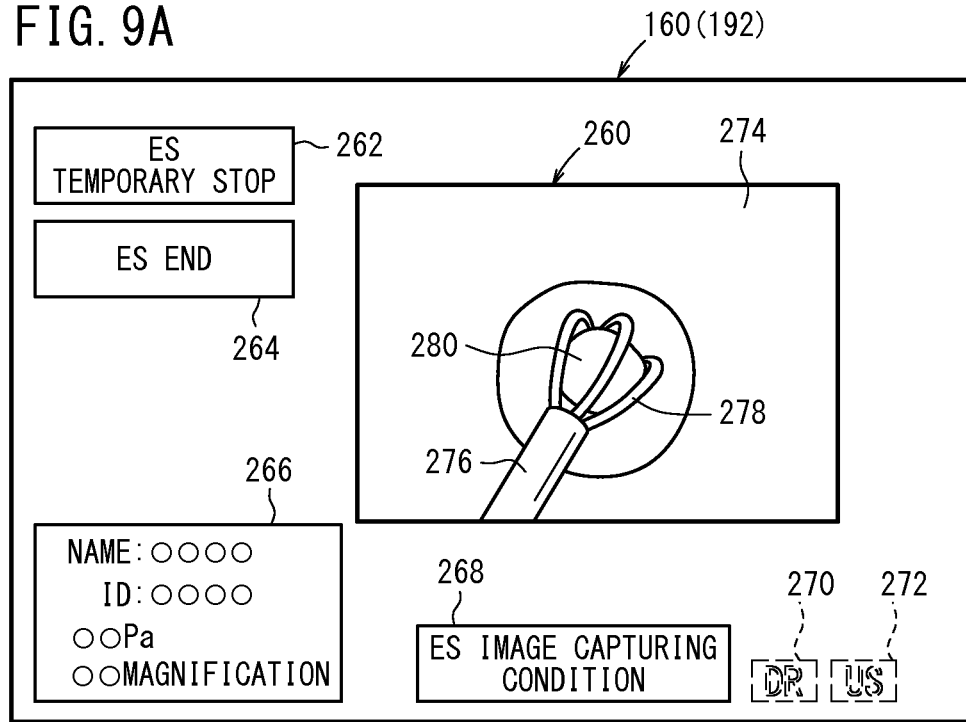
FIGS. 9A and 9B are explanatory views for illustrating the second specific function.

FIG. 9A is a view of contents displayed on the touch panel 150 in a case where the endoscope apparatus 32 is controlled to acquire the optical image of the patient 16.

An optical moving image 260, icons 262, 264, and 268 to 272, and an individual information display area 266 are displayed on the screen of the display portion 160. The moving image 260 contains a digestive organ 274 of the patient 16, a fiberscope 276 inserted into the digestive organ 274, a forceps 278 formed on the tip of the fiberscope 276, and a tissue 280 such as a polyp taken by the forceps 278.

The icon 262 is an operation icon for temporarily stopping (interrupting) the optical moving image capturing, and the icon 264 is an operation icon for ending the moving image capturing. The individual information display area 266 includes the name and ID of the patient 16, the pressure of air pumped into the digestive organ 274, and the magnification of the optical image. The icon 268 is an operation icon for changing the moving image capturing conditions (such as the pressure of the air pumped into the digestive organ 274 and the magnification of the optical image). The icon 270 is a selection icon, which the doctor 18 selects to control the radiation output apparatus 22 and the radiographic image capturing apparatus 24. The icon 272 is a selection icon, which the doctor 18 selects to control the ultrasonic diagnosis apparatus 30.

In FIG. 9A, for the purpose of controlling the endoscope apparatus 32 to acquire the optical image of the patient 16, the contents of the optical moving image capturing are displayed on the screen of the display portion 160, while the icons 270, 272 are shown by broken lines and cannot be selected.

The diagnosis or procedure currently on the patient 16 is the acquisition of the optical image of the patient 16 and the collection of the tissue 280. Therefore, the operation control portion 154 informs the display control portion 148 that only the icons 262, 264, 268 can be operated in FIG. 9A, and the display control portion 148 acts based on the information to show the icons 270, 272 using the broken lines on the screen of the display portion 160.

The icons 262, 264, 268, associated with the operation subjects of the endoscope apparatus 32, are larger displayed than the non-selectable icons 270, 272.

In a case where the doctor 18 operates the icon 268, the operation control portion 154 judges the operation on the icon 268 to be valid and sends information on the judgment to the display control portion 148. The display control portion 148 acts based on the information to display the contents for changing the image capturing conditions of the endoscope apparatus 32 on the display portion 160. Consequently, the doctor 18 can change the image capturing conditions and can operate the mobile apparatus 48 to control the endoscope apparatus 32.

Also in this case, to change the image capturing conditions, it is necessary to interrupt the moving image capturing. Therefore, in a case where the icon 262 for temporarily stopping the capturing is not operated and the icon 268 is operated, the operation control portion 154 sends the information on the judgment to the control portion 132, and the control portion 132 acts to send a command instructing to interrupt the moving image capturing from the communication portion 130 to the endoscope apparatus 32. In FIG. 9A, in a case where the doctor 18 operates the icon 270, 272 by mistake, the operation control portion 154 judges the operation by the doctor 18 to be invalid and sends information on the judgment to the display control portion 148.

In a case where the doctor 18 operates the icon 264, the operation control portion 154 judges that the operation on the icon 264 by the doctor 18 is valid as instructing to end the moving image capturing. The operation control portion 154 sends information on the judgment to the display control portion 148 and the control portion 132. The control portion 132 sends a command instructing to end the image capturing from the communication portion 130 to the endoscope apparatus 32 based on the information, and thereby acts to end the moving image capturing.

Figure 9B:
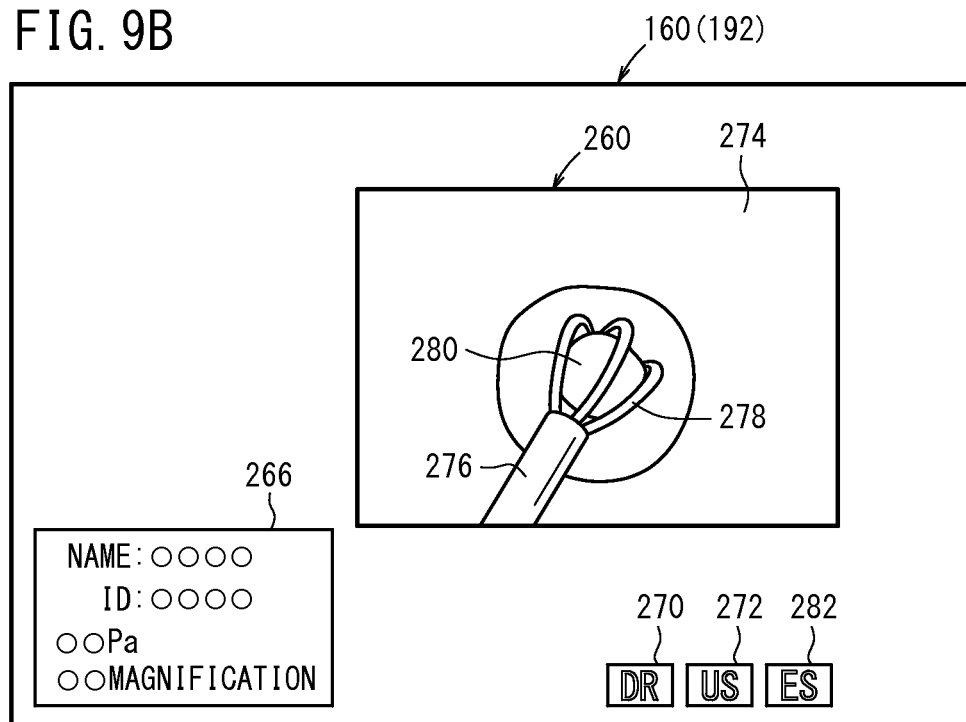

The display control portion 148 switches the contents displayed on the display portion 160 from FIG. 9A to FIG. 9B based on the information. In FIG. 9B, the moving image 260, the individual information display area 266, and three icons 270, 272, 282 are displayed on the display portion 160. In this case, lines representing the two icons 270, 272 are switched from the broken lines to solid lines. The icon 282 is a selection icon, which the doctor 18 selects to control the endoscope apparatus 32.

Also in this case, after the moving image capturing is ended, all the medical apparatuses in the operating room 12 are temporarily in the unused states. Therefore, the selectable icons 270, 272, 282 corresponding to all the medical apparatuses are displayed on the display portion 160. In a case where the doctor 18 operates one of the icons, the operation control portion 154 acts to control the control portion 132 and the display control portion 148, so that the medical apparatus corresponding to the operated icon that is to be controlled next and the contents corresponding to the medical apparatus can be displayed on the display portion 160.

Also in the second specific function, the signals can be transmitted and received between the mobile apparatus 48 and the console 52 via the wireless communication link. Therefore, the control portion 132 can send the contents displayed on the display portion 160 of the touch panel 150 from the communication portion 130 to the console 52 (see FIGS. 1, 2, and 4) via the wireless communication link. The display control portion 190 in the console 52 can receive the contents and can act to display the contents on the display portion 192.

In a case where the console 52 contains the transmission/reception setting portion 182, the display control portion 190, the information management portion 198, and the operation control portion 199 having the same functions as the transmission/reception setting portion 140, the display control portion 148, the information management portion 152, and the operation control portion 154, the doctor 18 or the technician 54 can operate the operation portion 194 to control the medical apparatuses in the operating room 12.

[Third Specific Function]

Concerning the third specific function, before the surgical operation on the patient 16 in the operating room 12, the information management portion 152 stores the public key or the secret key (encryption key) for the encryption processing in the encryption processing portion 142, and also the mobile apparatus 120a for the other medical expert in the medical institution acquires the encryption key in advance.

Then, the camera 34 is used for acquiring a camera image of the entire operating room 12 (such as an overhead view image of the entire operating room 12) or a camera image of a part of the operating room 12 (such as an image including the surgical operation on the patient 16 by the doctor 18), and sends the camera image to the mobile apparatus 48 via the wireless communication link. The radiographic image capturing apparatus 24 starts to acquire the radiographic image in the fluorography, and sends the radiographic image to the mobile apparatus 48 via the wireless communication link or via the optical fiber cable 58 and the console 52. The ultrasonic diagnosis apparatus 30 acquires the ultrasonic image, and sends the ultrasonic image to the mobile apparatus 48 via the wireless communication link. The endoscope apparatus 32 acquires the optical image, and sends the optical image to the mobile apparatus 48 via the wireless communication link.

In a case where the various information (such as the order information and the image capturing conditions) are connected to the moving images, also the information are sent from the apparatuses to the mobile apparatus 48. The encryption processing portion 142 in the mobile apparatus 48 receives the moving images (the camera image, the radiographic image, the ultrasonic image, and the optical image) and the various information connected thereto, and then acts to subject the information to the encryption processing. The image processing portion 144 acts to convert the moving images into the terrestrial digital television broadcast signals. The encrypted information and the moving images processed for the terrestrial digital television broadcasting are delivered in real time from the communication portion 130 to the predetermined area in the medical institution via the terrestrial digital television broadcasting.

Figure 10A:
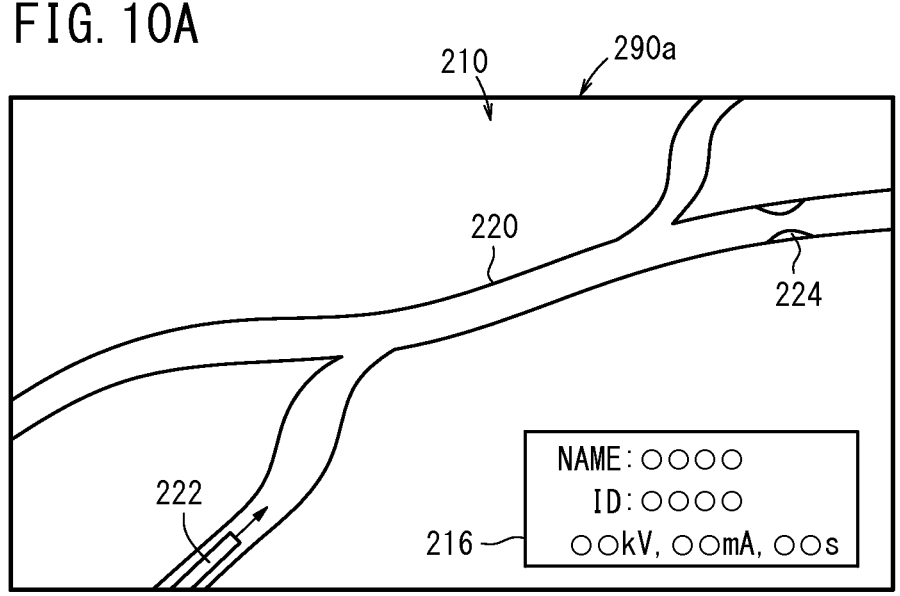
FIGS. 10A and 10B are explanatory views for illustrating a third specific function.
Figure 10B:
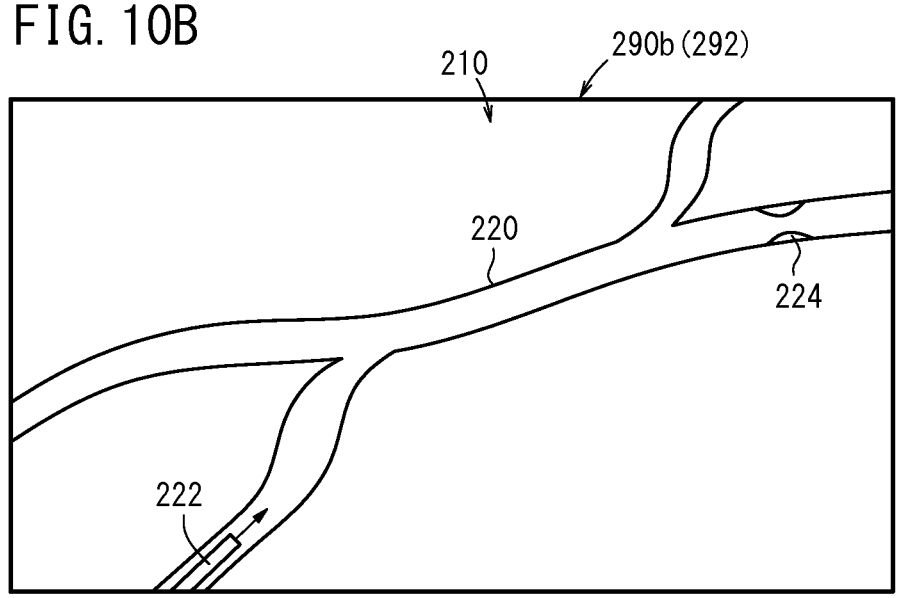

FIG. 10A is a view of contents displayed on a display portion 290a in the mobile apparatus 120a (see FIG. 2) for the medical expert in the predetermined area. FIG. 10B is a view of contents displayed on a display portion 290b in the mobile apparatus 120b for the family member of the patient 16 in the predetermined area or on a display portion 292 in the display apparatus 124 placed in the predetermined area.

In this case, since the mobile apparatus 120a for the medical expert acquires the encryption key in advance, the mobile apparatus 120a receives the moving images and the encrypted information delivered via the terrestrial digital television broadcasting, and decodes the encrypted information (connected to the moving images). Thus, the moving image 210 can be displayed on the screen of the display portion 290a, and the decoded information can be displayed in the individual information display area 216.

The mobile apparatus 120b for the family member of the patient 16 and the display apparatus 124 do not acquire the encryption key. Therefore, in a case where the mobile apparatus 120b and the display apparatus 124 receive the moving images and the encrypted information delivered via the terrestrial digital television broadcasting, the mobile apparatus 120b and the display apparatus 124 cannot decode the encrypted information and act to display only the moving image 210 on the screens of the display portions 290b, 292.

Also in the third specific function, the signals can be transmitted and received between the mobile apparatus 48 and the console 52 via the wireless communication link. Therefore, the control portion 132 may send the moving images and the encrypted information to be delivered by the terrestrial digital television broadcasting from the communication portion 130 to the console 52 via the wireless communication link. In a case where the encryption key is registered on the information management portion 198 in advance, the display control portion 190 in the console 52 can act to decode the encrypted information and to display the decoded information and the moving images on the display portion 192.

In a case where the console 52 contains the encryption processing portion 184 and the image processing portion 186 having the same functions as the encryption processing portion 142 and the image processing portion 144, acts to generate the information for the terrestrial digital television broadcasting (the moving images and the encrypted information) in the console 52, and utilizes the mobile apparatus 48 as the transponder, the console 52 can deliver the information to the predetermined area in real time via the terrestrial digital television broadcasting using the mobile apparatus 48.

Operation of Embodiment

Operation of the medical system 10 according to this embodiment will be described below.

First, a basic processing sequence of the medical system 10 (e.g. the fluorography or fluoroscopic image capturing performed during the surgical operation on the patient 16) will be described with reference to FIG. 11. Then, specific processing sequences according to this embodiment (using the first to third specific functions) will be described with reference to FIGS. 12A to 14.

The basic processing sequence of FIG. 11 includes the operation of the entire medical system 10 using the console 52 as the master before and during the fluorography. Thus, in FIG. 11, the technician 54 operates the console 52, based on an instruction from the doctor 18, to start or end the fluorography.

In FIGS. 11 to 14, the thinned image and the connected information are sent from the radiographic image capturing apparatus 24 to the mobile apparatus 48 via the wireless communication link, and the original radiographic image and the connected information are sent from the radiographic image capturing apparatus 24 via the optical fiber cable 58, the controller 102, and the console 52.

In FIGS. 11 to 14, the moving images and the various information are delivered in real time from the mobile apparatus 48 to the predetermined area via the terrestrial digital television broadcasting.

Furthermore, the processing sequences of FIGS. 11 to 14 will be described with reference also to FIGS. 1 to 10B as necessary.

Basic Processing Sequence of Embodiment

In step S1 of FIG. 11, the communication link between the apparatuses in the medical system 10 is set prior to the surgical operation on the patient 16 (see FIGS. 1 and 2).

Specifically, the transmission/reception setting portion 140 in the mobile apparatus 48 (see FIG. 3) allocates the predetermined channel to the radiographic image capturing apparatus 24, the ultrasonic diagnosis apparatus 30, the endoscope apparatus 32, the camera 34, and the console 52, to form the multiple wireless communication link of the communication portion 130 in the mobile apparatus 48 with the communication portion 100 in the radiographic image capturing apparatus 24, the communication portion 170 in the console 52 (see FIG. 4), the camera 34, the ultrasonic diagnosis apparatus 30, and the endoscope apparatus 32. Furthermore, the transmission/reception setting portion 140 selects the command to be sent to the apparatuses. In addition, the transmission/reception setting portion 140 sends the public key or the secret key (encryption key) for the encryption processing in the encryption processing portion 142 to the mobile apparatus 120a for the other medical expert, and pre-registers the mobile apparatus 120a. The information management portion 152 manages the allocated channel, the selected command, and the encryption key.

In step S2, in a case where the patient 16 is introduced to the operating room 12 and the surgical operation is performed therein, the camera 34 starts to capture the image of the operating room 12. The moving image of the operating room 12 captured using the camera 34 (at least the one-frame camera image) is sequentially sent to the mobile apparatus 48 via the wireless communication link. The image processing portion 144 in the mobile apparatus 48 receives the camera image, converts the camera image into the terrestrial digital television broadcast signals, and stores the processed camera image in the image memory 146.

In step S3, the control portion 132 starts to deliver the camera image stored in the image memory 146 from the communication portion 130 to the predetermined area in real time via the terrestrial digital television broadcasting. In the predetermined area, the mobile apparatuses 120a, 120b and the display apparatus 124 receive the camera image and act to display the image on the display portions 290a, 290b, 292. Consequently, the other medical expert and the family member of the patient 16 can watch the contents displayed on the display portions 290a, 290b, 292 to grasp the situation of the operating room 12. Since the mobile apparatus 48 delivers only the camera image of the operating room 12 without the individual information on the patient 16, only the image of the operating room 12 is displayed on the display portions 290*a*, 290*b*, 292.

The camera image, delivered in real time via the terrestrial digital television broadcasting, is displayed also on the display portion 160 in the mobile apparatus 48. Furthermore, also the console 52 can receive the camera image and can display the image on the display portion 192 or the display apparatus 36.

After the patient 16 is introduced to the operating room 12 and placed on the operating table 14, the doctor 18 starts to operate on the patient 16. As described above, the camera 34 continues to capture the image of the operating room 12 and delivers the camera image in real time via the terrestrial digital television broadcasting. Therefore, what goes on in the surgical operation on the patient 16 in the operating room 12 is displayed on the display portions 290*a*, 290*b* in the mobile apparatuses 120*a*, 120*b*, the display portion 292 in the display apparatus 124, the display portion 160 in the mobile apparatus 48, the display portion 192 in the console 52, and the display apparatus 36.

Consequently, the other medical expert and the family member of the patient 16 can grasp the surgical operation on the patient 16. In this embodiment, the mobile apparatuses 120*a*, 120*b* and the display apparatus 124 are authorized only to receive the camera image delivered from the mobile apparatus 48 and to display the camera image on the display portions 290*a*, 290*b*, 292. Therefore, the mobile apparatuses 120*a*, 120*b* and the display apparatus 124 cannot be used for remotely operating the medical apparatuses in the operating room 12 via the mobile apparatus 48.

In a case where the doctor 18 recognizes the need for the fluorography during the surgical operation on the patient 16, the doctor 18 verbally instructs the technician 54 to start the fluorography.

The technician 54 receives the instruction from the doctor 18, and operates the operation portion 194 in the console 52. Then, the control portion 174 acquires the order information from the RIS 112 or the HIS 114, and acts to store the acquired order information in the order information storage portion 176 (step S4).

In step S5, in response to the operation on the operation portion 194 by the technician 54, based on the order information including the information on the imaging area of the patient 16, the image capturing procedure, the radiation output apparatus 22, and the radiographic image capturing apparatus 24, the control portion 174 acts to set the image capturing conditions (including the tube voltage, the tube current, and the irradiation time) for applying the radiation 20 from the radiation source 106 in the radiation output apparatus 22 to the imaging area of the patient 16, and acts to store the preset image capturing conditions and the order information in the image capturing condition storage portion 178.

In step S6, the technician 54 interposes the radiographic image capturing apparatus 24 between the patient 16 and the operating table 14, and positions the imaging area of the patient 16 correctly with respect to the radiation output apparatus 22 and the radiographic image capturing apparatus 24.

In this case, the control portion 108 in the radiation output apparatus 22 requests the console 52 to send the image capturing conditions and the like. The control portion 132 receives the request sent from the radiation output apparatus 22 via the communication portion 172, and acts to send the image capturing conditions stored in the image capturing condition storage portion 178 from the communication portion 172 to the control portion 108 in response to the request.

In a case where the battery 92 supplies electric energy to the cassette control portion 82 and the communication portion 94 in the radiographic image capturing apparatus 24, the cassette control portion 82 requests the console 52 to send the order information and the like via the communication portion 94. The control portion 132 receives the request sent from the cassette control portion 82 via the communication portion 172, and acts to send the order information and the image capturing conditions stored in the image capturing condition storage portion 178 from the communication portion 172 to the radiographic image capturing apparatus 24 in response to the request. The cassette control portion 82 acts to store the order information and the image capturing conditions sent via the communication portion 94 in the information storage portion 88. In a case where the battery 92 applies a voltage to the pixels in the radiation conversion panel 80, the pixels can convert the radiation 20 into the electric charges and can store the electric charges.

In a case where the battery 156 in the mobile apparatus 48 supplies the electric energy to the components in the mobile apparatus 48, also the control portion 132 requests the console 52 to send the order information and the like via the communication portion 130. The control portion 132 receives the request sent via the communication portion 170, and acts to send the order information and the image capturing conditions stored in the image capturing condition storage portion 178 from the communication portion 170 to the mobile apparatus 48 in response to the request. The control portion 132 acts to store the order information sent via the communication portion 130 in the order information storage portion 134 and to store the order information and the image capturing conditions in the image capturing condition storage portion 136.

After the preparation for the image capturing including the positioning of the patient 16 is completed, the technician 54 turns on the exposure switch 196. Then, the control portion 174 generates the synchronization control signal for synchronizing the start of the radiation 20 output from the radiation source 106 with the detection of the radiation 20 and the conversion to the radiographic image in the radiation conversion panel 80, thereby performing the radiographic image capturing in the imaging area of the patient 16. The control portion 174 sends the generated synchronization control signal (command) from the communication portion 172 to the radiation output apparatus 22, and sends the signal from the communication portion 170 to the radiographic image capturing apparatus 24 and the mobile apparatus 48 via the wireless communication link.

The control portion 108 in the radiation output apparatus 22 receives the synchronization control signal, and acts to apply the radiation 20 with a predetermined dose from the radiation source 106 to the imaging area of the patient 16 for a predetermined irradiation time under the image capturing conditions (step S7).

The radiation 20 is transmitted through the imaging area of the patient 16 and reaches the radiation conversion panel 80 in the radiographic image capturing apparatus 24. In the case of using the direct-conversion-type radiation conversion panel 80, the radiation 20 is directly converted into the electric charges by the radiation conversion layer containing the a-Se or the like, and the electric charges are stored in the pixels. In the case of using the indirect-conversion-type radiation conversion panel 80, the radiation 20 is converted into the fluorescence by the scintillator, the fluorescence is converted into the electric charges by the photoelectric transducers in the pixels, and the electric charges are stored in the pixels.

The cassette control portion 82 receives the synchronization control signal via the communication portion 94, the control signal is supplied to the radiation conversion panel 80, and the electric charges corresponding to the radiographic image of the patient 16, stored in the pixels, are read out as the electric signals. Thus, the cassette control portion 82 acts to sequentially read out the electric charges stored in the pixels arranged in the matrix line by line and to temporarily store the electric signals corresponding to the read electric charges as the one-frame radiographic image in the frame memory 84 (step S8).

In step S9, the connection processing portion 90 connects the one-frame radiographic image stored in the frame memory 84 with the cassette ID information, the order information, and the image capturing conditions stored in the information storage portion 88. The connected radiographic image, the cassette ID information, the order information, and the image capturing conditions are stored in the image storage portion 86 (step S10).

In step S11, the cassette control portion 82 transfers the radiographic image, the cassette ID information, the order information, and the image capturing conditions stored in the image storage portion 86 to the controller 102 via the communication portion 94 and the optical fiber cable 58a, and outputs them to the signal processing portion 98.

In the signal processing portion 98, the radiographic image is subjected to the predetermined thinning processing to obtain the thinned image. The communication portion 100 sends the thinned image, the cassette ID information, the order information, and the image capturing conditions to the mobile apparatus 48 via the wireless communication link.

In a case where the communication portion 130 in the mobile apparatus 48 receives the thinned image and the various information connected thereto (including the cassette ID information, the order information, and the image capturing conditions) sent from the radiographic image capturing apparatus 24, the control portion 132 acts to store the thinned image and the various information connected thereto in the image memory 146. The display control portion 148 acts to display the thinned image and the various information connected thereto stored in the image memory 146 on the display portion 160 (step S12). The doctor 18 can watch the contents displayed on the display portion 160, and thereby can rapidly grasp the state of the imaging area in the patient 16.

The controller 102 receives the radiographic image and the various information connected thereto (including the cassette ID information, the order information, and the image capturing conditions) via the optical fiber cable 58a, stores them in the storage portion 104, and sends them to the console 52 via the optical fiber cable 58b. The control portion 174 in the console 52 receives the radiographic image and the various information connected thereto via the communication portion 172, stores them in the image memory 188, and acts to display them on the display portion 192 (step S12). The technician 54 can watch the contents displayed on the display portion 192, and thereby can grasp the state of the imaging area in the patient 16, the quality of the radiographic image, etc.

The control portion 174 in the console 52 acts to transfer the radiographic image and the various information connected thereto stored in the image memory 188 from the communication portion 170 to the mobile apparatus 48 via the wireless communication link. In a case where the communication portion 130 in the mobile apparatus 48 receives the radiographic image and the various information connected thereto transferred from the radiographic image capturing apparatus 24, the control portion 132 temporarily stores the radiographic image and the various information in the image memory 146. The display control portion 148 controls the display portion 160, so that the original radiographic image and the various information connected thereto are displayed instead of the thinned image and the various information connected thereto (step S12). The doctor 18 can watch the display portion 160, and thereby can grasp the detail of the imaging area in the patient 16, the quality of the radiographic image, etc.

Then, the image processing portion 144 converts the radiographic image into the terrestrial digital television broadcast signals, while the encryption processing portion 142 encrypts the various information connected to the radiographic image using the encryption key managed in the information management portion 152. The control portion 132 stores the radiographic image for the terrestrial digital television broadcasting and the encrypted various information in the image memory 146, and delivers the radiographic image and the encrypted various information from the communication portion 130 to the predetermined area in real time via the terrestrial digital television broadcasting. The processings performed in the receivers of the mobile apparatuses 120a, 120b and the display apparatus 124 will be hereinafter described using FIG. 14.

In step S13, in a case where the fluorography is continued (step S13: NO), the medical system 10 goes back to step S7, and the next radiation 20 emission is performed. Thus, the moving image of the imaging area in the patient 16 (the radiographic images in a plurality of frames) can be acquired by repeating the processes of steps S7 to S13.

In step S13, in a case where the fluorography is completed (step S13: YES), the doctor 18 verbally instructs the technician 54 to end the fluorography. The technician 54 operates the operation portion 194 based on the instruction from the doctor 18, the control portion 174 sends a command instructing to end the fluorography from the communication portion 172 to the radiation output apparatus 22, and the control portion 174 further sends the command from the communication portion 170 to the radiographic image capturing apparatus 24 and the mobile apparatus 48 via the wireless communication link. Then, the control portion 108 acts to stop the radiation 20 output from the radiation source 106 based on the sent command. Consequently, the radiographic image delivery via the terrestrial digital television broadcasting is ended.

The surgical operation on the patient 16 may be continued even after the end of the fluorography. Therefore, the technician 54 does not remove the radiographic image capturing apparatus 24 interposed between the patient 16 and the operating table 14, and maintains the correct position of the patient 16.

After the surgical operation on the patient 16 is ended and the patient 16 leaves the operating table 14 in the operating room 12, the image capturing using the camera 34 in the operating room 12 is stopped (step S14: YES), and thus the camera image delivery via the terrestrial digital television broadcasting is stopped.

[Processing Sequence Using First Specific Function]

The processing sequence using the first specific function will be described with reference to FIGS. 12A to 12C.

Figure 12A:
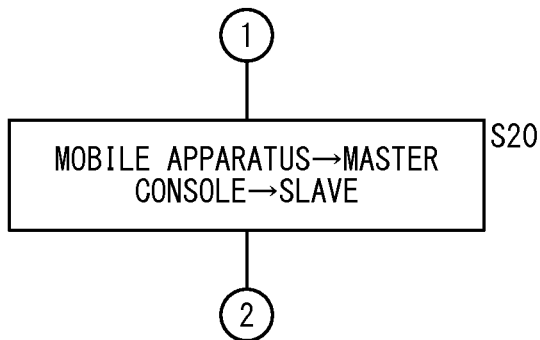
FIGS. 12A to 12C are flowcharts for illustrating the first specific function.
Figure 12B:
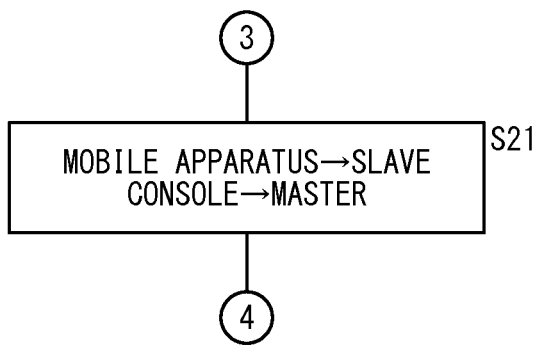
Figure 12C:
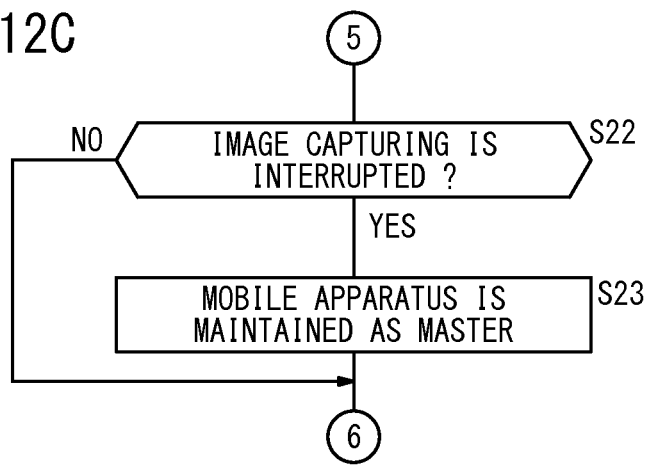

Immediately after the fluoroscopic image is started in step S7 of FIG. 11, the switch processing portion 180 in the console 52 (see FIG. 4) switches the master for controlling the radiation output apparatus 22 and the radiographic image capturing apparatus 24 (see FIGS. 1 and 2) from the console 52 to the mobile apparatus 48 and switches the slave from the mobile apparatus 48 to the console 52 in step S20 of FIG. 12A. The switch processing portion 180 sends the information on the switching between the master and the slave at the start of the fluorography from the communication portion 170 to the switch processing portion 138 in the mobile apparatus 48 (see FIG. 3) via the wireless communication link. The control portion 174 controls the components in the console 52 to prevent the processings by the operation on the operation portion 194 or the like by the technician 54 (to invalidate the operation by the technician 54).

In a case where the communication portion 130 receives the information sent from the switch processing portion 180, the mobile apparatus 48 can recognize that the mobile apparatus 48 is switched to the master after the start of the fluorography. The control portion 132 controls the components in the mobile apparatus 48 based on the information, so that the doctor 18 can operate the mobile apparatus 48. After step S20, the processings of step S8 and the following steps of FIG. 11 are carried out in the medical system 10.

In a case where the doctor 18 operates the icon 214 (see FIGS. 6A and 7A) or the command instructing to end the fluorography is sent to the radiographic image capturing apparatus 24 and the console 52 in response to the operation on the icon 214 (step S13: YES), the switch processing portion 138 in the master of the mobile apparatus 48 judges that the fluorography is completed, switches the mobile apparatus 48 to the slave based on the judgment, and switches the console 52 to the master in next step S21 of FIG. 12B. Then, the switch processing portion 138 sends the information on the switching between the master and the slave at the end of the fluorography from the communication portion 130 to the switch processing portion 180 in the console 52 via the wireless communication link. The control portion 132 controls the components in the mobile apparatus 48 to prevent the processings by the operation on the operation portion 162 or the like by the doctor 18 (to invalidate the operation by the doctor 18).

In a case where the communication portion 170 receives the information sent from the switch processing portion 138, the console 52 can recognize that the console 52 is switched to the master after the end of the fluorography. The control portion 174 controls the components in the console 52 based on the information, so that the technician 54 can operate the console 52.

The radiographic image is displayed on the display portion 192 in the mobile apparatus 48 and the like in step S12. In a case where the displayed radiographic image is not clear to the doctor 18, the doctor 18 decides to interrupt the fluorography and operates the icon 212, so that the image capturing conditions are reset and the patient 16 is correctly positioned (step S22: YES).

In this case, the doctor 18 may continuously operate the mobile apparatus 48 during the interruption of the fluorography, and therefore the switch processing portion 138 maintains the mobile apparatus 48 as the master (step S23). The control portion 132 in the mobile apparatus 48 sends the command instructing to interrupt the radiation 20 emission from the communication portion 130 to the radiographic image capturing apparatus 24 via the wireless communication link, and sends the command to the radiation output apparatus 22 via the console 52. The control portion 108 receives the command, and acts to interrupt the radiation 20 output from the radiation source 106 based on the command.

During the interruption of the fluorography, the technician 54 performs the positioning of the patient 16 in response to the verbal instruction from the doctor 18 (step S6) or the doctor 18 operates the operation portion 162 in the mobile apparatus 48 to reset the image capturing conditions (step S5). In a case where incorrect order information is set, the doctor 18 may operate the operation portion 162 in the mobile apparatus 48 to reset the order information (step S4).

After these processings, in a case where the doctor 18 operates the icon 226, the control portion 132 acts to send the command instructing to restart the radiation 20 emission (under the changed image capturing conditions) from the communication portion 130 to the radiographic image capturing apparatus 24 via the wireless communication link, and further acts to send the command from the console 52 to the radiation output apparatus 22. Consequently, the control portion 108 receives the command and acts to restart the radiation 20 output from the radiation source 106 based on the command (under the changed image capturing conditions) (step S7).

[Processing Sequence Using Second Specific Function]

Figure 13:
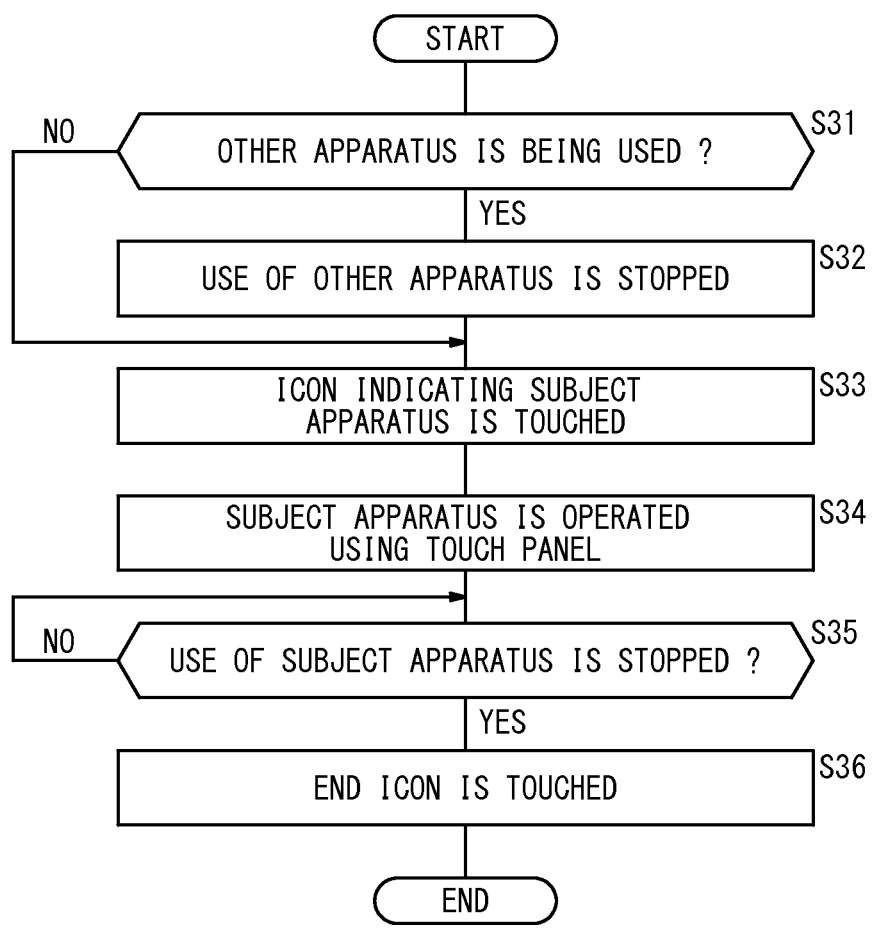
FIG. 13 is a flowchart for illustrating the second specific function.

The processing sequence using the second specific function will be described with reference to FIG. 13.

First, so that the doctor 18 (see FIGS. 1 and 5) can use a particular medical apparatus, in a case where another medical apparatus is being used at the moment (step S31: YES), the doctor 18 operates the operation portion 162 (the icon 214 in FIGS. 6A and 7A, the icon 244 in FIG. 8A, or the icon 264 in FIG. 9A) to stop the use of the other medical apparatus (step S32).

Thus, in step S32, the control portion 132 in the mobile apparatus 48 acts to send a command instructing to stop the moving image capturing from the communication portion 130 to the other medical apparatus via the wireless communication link. The other medical apparatus receives the command and acts to stop the moving image capturing based on the command.

Consequently, all the medical apparatuses in the operating room 12 are made operational, the contents displayed on the display portion 160 are switched to those of FIG. 7B, 8B, or 9B. FIG. 7B is a view of the contents displayed after the stop of the radiation output apparatus 22 and the radiographic image capturing apparatus 24, FIG. 8B is a view of the contents displayed after the stop of the ultrasonic diagnosis apparatus 30, and FIG. 9B is a view of the contents displayed after the stop of the endoscope apparatus 32.

In next step S33, the doctor 18 operates the icon indicating the particular medical apparatus (one of the icons 232 to 236, 250, 252, 256, 270, 272, and 282). Then, the operation control portion 154 judges the icon operation by the doctor 18 to be valid and sends information on the selection of the particular medical apparatus to the control portion 132 and the display control portion 148. The control portion 132 informs the particular medical apparatus that the apparatus is selected as the control subject from the communication portion 130 via the wireless communication link. Furthermore, the display control portion 148 acts to display the contents for operating the particular medical apparatus on the display portion 160.

Consequently, the doctor 18 can operate the operation portion 162 to control the particular medical apparatus in next step S34. In a case where the doctor 18 operates the operation portion 162 (the icon indicating the particular medical apparatus), the operation control portion 154 judges the icon operation by the doctor 18 to be valid and sends information on the operation to the control portion 132 and the display control portion 148.

The control portion 132 sends a command corresponding to the information from the communication portion 130 to the particular medical apparatus via the wireless communication link. The particular medical apparatus acquires the moving image in response to the command, and sends the acquired moving image to the mobile apparatus 48 via the wireless communication link. The mobile apparatus 48 can display the received moving image on the display portion 160. Meanwhile, the display control portion 148 controls the display portion 160 to display the contents corresponding to the information.

In a case where the use of the particular medical apparatus is stopped in next step S35 (step S35: YES), the doctor 18 may operate the operation portion 162 (the icon 214, 244, 264) to stop the use of the particular medical apparatus in the same manner as step S32 (step S36). Thus, the control portion 132 acts to send a command instructing to stop the moving image capturing from the communication portion 130 to the particular medical apparatus via the wireless communication link. The particular medical apparatus receives the command and acts to stop the moving image capturing based on the command.

In a case where the other medical apparatus is continuously used after step S31 (step S31: NO), the other medical apparatus may be subjected to the processings of step S33 and the following steps without step S32. In this case, the term "the particular medical apparatus" may be replaced by "the other medical apparatus" in the above description of steps S33 to S36. Therefore, description of step S33 to S36 using the other medical apparatus is omitted.

[Processing Sequence Using Third Specific Function]

The processing sequence using the third specific function will be described with reference to FIG. 14.

The real-time delivery of the moving image and the encrypted information (connected to the moving image) from the mobile apparatus 48 to the predetermined area via the terrestrial digital television broadcasting is described above using FIG. 11. Therefore, the processings in the receivers of the mobile apparatuses 120a, 120b and the display apparatus 124 will be described below.

First, in step S41, the mobile apparatus 120a receives the moving image and the encrypted information in the predetermined area. In a case where the reception is the first reception (step S42: NO) and the encryption key (such as a password) is pre-registered on the mobile apparatus 120a (step S43: YES), for example, a password entry screen is displayed on the display portion 290a to request the other medical expert possessing the mobile apparatus 120a to input the password.

In step S44, the other medical expert operates the mobile apparatus 120a to input the password. In a case where the input password corresponds to the pre-registered password, the mobile apparatus 120a acts to decode the encrypted information (step S45) and to display the moving image and the decoded information on the display portion 290a (step S46, FIG. 10A). Therefore, the other medical expert can watch the contents displayed on the display portion 290a to grasp the moving image and the individual information of the patient 16 (including the order information and the image capturing conditions).

In a case where the terrestrial digital television broadcasting is not ended (step S47: NO) and the mobile apparatus 120a receives the next moving image and the encrypted information (step S41), the reception is the second reception (step S42: YES). Therefore, the processings of steps S45 and S46 are performed without the password input.

Thus, until the terrestrial digital television broadcasting is ended (step S47: YES), the processings of steps S41, S42, and S45 to S47 are repeated in the mobile apparatus 120a.

In a case where the mobile apparatus 120b or the display apparatus 124 receives the moving image and the encrypted information in the predetermined area (step S41) and the reception is the first reception (step S42: NO), since the password is not pre-registered on the mobile apparatus 120b and the display apparatus 124 (step S43: NO), the encrypted information cannot be decoded, and only the moving image is displayed on the display portion 290b, 292 (step S48, FIG. 10B). Therefore, the family member of the patient 16 can watch the contents displayed on the display portion 290b, 292 to grasp the moving image of the patient 16.

In a case where the terrestrial digital television broadcasting is not ended (step S47: NO) and the mobile apparatus 120b or the display apparatus 124 receives the next moving image and the encrypted information (step S41), the reception is the second reception (step S42: YES). Therefore, the processing of step S48 is continuously performed in the mobile apparatus 120b or the display apparatus 124.

Thus, until the terrestrial digital television broadcasting is ended (step S47: YES), the processings of steps S41, S42, S48, and S47 are repeated in the mobile apparatus 120b or the display apparatus 124.

Advantageous Effects of Embodiment

As described above, the medical system 10 of this embodiment has the first to third specific functions and thereby shows the following advantageous effects.

Advantageous Effects Due to First Specific Function

In the first specific function, the apparatus (master) for controlling the radiation output apparatus 22 and the radiographic image capturing apparatus 24 is switched from the console 52 to the mobile apparatus 48 after the start of the fluorography. Thus, the mobile apparatus 48 and the console 52 are the master and the slave for controlling the radiation output apparatus 22 and the radiographic image capturing apparatus 24. The console 52 is the master and the mobile apparatus 48 is the slave before the start of the fluorography, and the console 52 is switched to the slave and the mobile apparatus 48 is switched to the master after the start of the fluorography.

Therefore, for example, the doctor 18 does not have to verbally instruct the technician 54 to interrupt the fluorography and to reset the image capturing conditions. The doctor 18 can operate the switched master of the mobile apparatus 48 placed in the vicinity of the patient 16 (close to the doctor 18), and thereby can reset the image capturing conditions rapidly and appropriately. In a case where the body of the patient 16 is moved, the doctor 18 gives a verbal instruction to the technician 54, and the technician 54 performs only the positioning of the patient 16 based on the instruction during the interruption of the fluorography. Consequently, the workload of the technician 54 can be reduced, and the positioning can be rapidly performed.

Thus, in the first specific function, the procedures including the change of the image capturing conditions and the positioning of the patient 16 after the start of the fluorography can be rapidly and appropriately performed, and the fluorography can be rapidly restarted after the interruption.

The master is switched from the mobile apparatus 48 to the console 52 by the switch processing portion 138, 180 after the fluorography is ended. Therefore, the technician 54 can operate the switched master of the console 52 to set the image capturing conditions and the like for the next fluorography.

The switch processing portion 138, 180 acts to maintain the mobile apparatus 48 as the master during the interruption of the fluorography, so that the doctor 18 can operate the mobile apparatus 48 during the interruption. Thus, the console 52 is maintained as the slave until the fluorography is ended.

In the case of using the mobile apparatus 48 as the master, the doctor 18 operates the touch panel 150 in the mobile apparatus 48, and the radiation output apparatus 22 and the radiographic image capturing apparatus 24 are controlled in response to the operation. Thus, the doctor 18 can operate the touch panel 150 to easily reset the image capturing conditions. Since the touch panel 150 does not have a concave-convex surface, the surface of the touch panel 150 can be subjected to a sterilization treatment after the surgical operation to keep the surface clean and to prevent in-hospital infection.

The mobile apparatus 48 and the console 52 have the switch processing portions 138, 180 respectively, and the mobile apparatus 48 and the console 52 can send signals to and receive signals from each other via the wireless communication link. Therefore, the mobile apparatus 48 and the console 52 can be rapidly switched between the master and the slave. Furthermore, in the case of using the mobile apparatus 48 as the master, the mobile apparatus 48 can control the radiation output apparatus 22 and the radiographic image capturing apparatus 24 using the console 52 as the transponder.

The communication portion 94 in the radiographic image capturing apparatus 24 and the console 52 send signals to and receive signals from each other via the wired communication link using the optical fiber cable 58, and the communication portion 100 in the radiographic image capturing apparatus 24 and the mobile apparatus 48 send signals to and receive signals from each other via the wireless communication link. In this case, the communication portion 94 sends the original radiographic image stored in the image storage portion 86 to the console 52, and the communication portion 100 sends the thinned image (generated by thinning the radiographic image in the signal processing portion 98) to the mobile apparatus 48 via the wireless communication link.

The thinned image has a smaller data amount (is formed at a lower frame rate with a smaller information amount) as compared with the radiographic image. Therefore, in the case of generating thinned image, the moving image (the thinned image) can be sent from the radiographic image capturing apparatus 24 to the mobile apparatus 48 via the wireless communication link. Consequently, the thinned image can be rapidly displayed on the display portion 160 of the mobile apparatus 48.

The original radiographic image may be sent from the radiographic image capturing apparatus 24 to the console 52 via the wired communication link without the thinning processing. In this case, the radiographic image can be displayed on the display portion 192 of the console 52 and the display apparatus 36, and the radiographic image can be stored in the storage portion 104 in the controller 102. In addition, in a case where the console 52 is used as the master, the console 52 can directly control the radiographic image capturing apparatus 24 via the communication portion 94. On the other hand, in a case where the mobile apparatus 48 is used as the master, the mobile apparatus 48 can directly control the radiographic image capturing apparatus 24 via the communication portion 100.

In a case where there is a defect in the signal transmission/reception between the communication portion 94 and the console 52 via the optical fiber cable 58, thereby failing to store the radiographic image in the storage portion 104, the radiographic image can be stored in the image storage portion 86 in the radiographic image capturing apparatus 24. Furthermore, the original radiographic image can be sent from the radiographic image capturing apparatus 24 through the mobile apparatus 48 to the console 52 via the wireless communication link. In a case where the defect of the signal transmission/reception via the optical fiber cable 58 is not eliminated even after switching the master to the console 52, the console 52 can control the radiographic image capturing apparatus 24 using the mobile apparatus 48 as the transponder.

Advantageous Effects Due to Second Specific Function

In the second specific function, the doctor 18 operates the operation portion 162 in the mobile apparatus 48, the signal corresponding to the operation (the command for controlling the operation subject medical apparatus) is sent from the communication portion 130 to the medical apparatus, and the medical apparatus is controlled based on the sent signal. In a case where the doctor 18 operating on the patient 16 in the operating room 12 cannot give verbal instructions to the operator (such as the technician 54) of the medical apparatus or cannot directly operate the medical apparatuses less sterilized as compared with the surgical tools, the doctor 18 can operate the operation portion 162 in the mobile apparatus 48 in hand to remotely control the medical apparatuses. Thus, the mobile apparatus 48 can be used as the remote controller for the medical apparatuses. The doctor 18 can operate the mobile apparatus 48 in hand, and thereby can remotely control the desired medical apparatus rapidly and appropriately, depending on the progress of the surgical operation.

In the second specific function, the medical apparatus, which is controlled by the operation on the operation portion 162 by the doctor 18, is limited by the operation control portion 154. Therefore, the doctor 18 can reliably operate the adequate medical apparatus suitable for the diagnosis or procedure on the patient 16.

A large number of the medical apparatuses are arranged in the operating room 12, and a plurality of the medical apparatuses are not used simultaneously in view of smoothly performing the surgical operation on the patient 16. In the case one of the medical apparatuses is used, the operation control portion 154 acts to make valid the operation for the one medical apparatus by the doctor 18 and to make invalid the operation for the other medical apparatuses on the operation portion 162 by the doctor 18. Therefore, the doctor 18 can remotely control the operation subject of the one medical apparatus, and can be reliably prevented from remotely controlling the other medical apparatuses by mistake.

The mobile apparatus 48 has the touch panel 150 containing the display portion 160 and the operation portion 162. In this case, the operation portion 162 is displayed on the screen of the touch panel 150 to indicate at least one of the medical apparatuses and the operation contents for the apparatuses. The operation portion 162 is the widget including the icons 204, 212, 214, 226, 230 to 236, 242, 244, 248 to 252, 256, 262, 264, 268, 270, 272, and 282, the text box display area 228, and the like for the medical apparatuses, which can be operated by the doctor 18. The operation control portion 154 acts to make valid the operation for the one medical apparatus on the icon or the like by the doctor 18 and to make invalid the operation for the other medical apparatuses on the icon or the like by the doctor 18.

The operation contents for the medical apparatus are displayed as the widget including the icon and the text box on the display portion 160 of the touch panel 150 in this manner. Therefore, the doctor 18 can operate the widget to easily remote-control the desired medical apparatus. In a case where the doctor 18 operates the widget corresponding to the other medical apparatus which is not in use, the operation is judged to be invalid, and the other medical apparatus can be reliably prevented from being controlled by mistake.

In a case where the widget for the desired medical apparatus in use is larger than the widget for the other medical apparatus not in use on the display portion 160, the doctor 18 can easily operate the widget for the desired medical apparatus.

The end icon 214, 244, 264, for stopping the control of the desired medical apparatus by the mobile apparatus 48, may be displayed on the display portion 160. In a case where the doctor 18 operates the icon 214, 244, 264, the operation control portion 154 acts to make valid the operations on the icons 232 to 236, 250, 252, 256, 270, 272, and 282 for the medical apparatuses. Consequently, the doctor 18 can operate the icons 232 to 236, 250, 252, 256, 270, 272, and 282 to select the next medical apparatus.

After the operations on the icons 232 to 236, 250, 252, 256, 270, 272, and 282 by the doctor 18 are made valid, in a case where the doctor 18 operates the icon for one medical apparatus, the operation control portion 154 judges that the one medical apparatus corresponding to the operated icon is newly used in the next step. The operation control portion 154 sends the signal corresponding to the judgment from the communication portion 130 to the selected medical apparatus, and acts to make invalid the operations on the icons for the other medical apparatuses by the doctor 18.

A large number of the medical apparatuses are placed in the operating room 12 as described above, and it is necessary to reliably send the signal (command) from the communication portion 130 to one of the medical apparatuses. Therefore, in the mobile apparatus 48, the transmission/reception setting portion 140 forms the multiple wireless communication link for the signal transmission/reception between the communication portion 130 and the medical apparatuses in advance before the control of the medical apparatuses.

In a case where the multiple communication link for the signal transmission/reception is formed in advance, the signal transmission/reception can be reliably performed via the wireless communication link between the communication portion 130 and the one medical apparatus within a limited frequency range (e.g. of 2.4 to 2.56 GHz).

In a case where the radiation output apparatus 22 and the radiographic image capturing apparatus 24 are being used, the mobile apparatus 48 sends the signal corresponding to the operation on the operation portion 162 from the communication portion 130 to the console 52 via the wireless communication link, and thereby controls the radiation output apparatus 22 and the radiographic image capturing apparatus 24 via the console 52. Thus, the mobile apparatus 48 can control the radiation output apparatus 22 and the radiographic image capturing apparatus 24 using the console 52 as the transponder.

Alternatively, the mobile apparatus 48 may send the signal from the communication portion 130 to the radiographic image capturing apparatus 24 and may send the signal from the communication portion 130 to the radiation output apparatus 22 via the console 52, to control the radiation output apparatus 22 and the radiographic image capturing apparatus 24. In this case also, the mobile apparatus 48 can directly control the radiographic image capturing apparatus 24, and can control the radiation output apparatus 22 using the console 52 as the transponder.

Advantageous Effects Due to Third Specific Function

In third specific function, the moving image associated with the diagnosis or the procedure on the patient 16 can be delivered to the predetermined area in real time via the terrestrial digital television broadcasting (or the area one-segment broadcasting in our country).

In a case where the doctor 18 operates on the patient 16 in the operating room 12, the camera 34 captures the moving image (the camera image) of the operating room 12, and the radiographic image capturing apparatus 24, the ultrasonic diagnosis apparatus 30, and the endoscope apparatus 32 capture the moving images of the internal site in the patient 16 (the radiographic image, the ultrasonic image, and the optical image associated with the diagnosis or procedure on the patient 16). The communication portion 130 in the mobile apparatus 48 can deliver the moving images to the mobile apparatus 120b capable of receiving the terrestrial digital television broadcasting (such as a mobile phone) for the family member of the patient 16 waiting in the predetermined area (such as the waiting room) in the medical institution, the mobile apparatus 120a capable of receiving the terrestrial digital television broadcasting (such as a mobile phone) for the other medical expert (such as a doctor, a resident, or a student) in the predetermined area (such as the operating room 12, the preparation room 50, or the meeting room) in the medical institution, and the display apparatus 124 (such as the display device) placed in the predetermined area.

Thus, the moving images can be delivered via live broadcasting to the family member of the patient 16 and the other medical expert. Therefore, it can be clarified whether the surgical operation on the patient 16 is appropriately performed or not. Furthermore, in a case where the family member of the patient 16 and the other medical expert stay in the same room, the family member can receive an appropriate explanation on the progress, etc. of the surgical operation on the patient 16 from the other medical expert while watching the moving image displayed on the display portion 290b of the mobile apparatus 120b or the display portion 292 of the display apparatus 124. In addition, the other medical expert can give an appropriate advice to the doctor 18.

In the third specific function, the situation of the diagnosis or procedure on the patient 16 in the operating room 12 can be delivered to the family member of the patient 16 and the other medical expert in the predetermined area in real time via the broadcasting in this manner.

The communication portion 130 in the mobile apparatus 48 receives the radiographic image from the radiographic image capturing apparatus 24 directly via the wireless communication link or from the radiographic image capturing apparatus 24 through the optical fiber cable 58 and the console 52 via the wireless communication link. In any case, the mobile apparatus 48 acts as the transponder for the terrestrial digital television broadcasting.

In a case where the communication portion 130 delivers the moving image and various types of the encrypted information to the predetermined area in real time via the broadcasting, the mobile apparatus 120*a* in the predetermined area can decode the encrypted information and display the moving image and the information, while the mobile apparatus 120*b* and the display apparatus 124 can display only the moving image. Therefore, only the other medical expert can watch the moving image and the encrypted individual information, while the family member of the patient 16 can watch only the moving image. Thus, a third person can be prevented from accessing to the individual information using a mobile phone.

The mobile apparatus 48, which conducts the terrestrial digital television broadcasting, is disposed on the table 46 slightly away from the patient 16. Therefore, the influence of the airwaves for the terrestrial digital television broadcasting on the patient 16 can be reduced, and the broadcasting airwaves can be prevented from being disturbed by the patient 16.

The terrestrial digital television broadcasting is performed not by the various medical apparatuses in the operating room 12 but by the mobile apparatus 48. Therefore, it is possible to reduce the influence of the airwaves for the terrestrial digital television broadcasting on the portable radiographic image capturing apparatus 24, the ultrasonic diagnosis apparatus 30, the endoscope apparatus 32, and the batteries in these medical apparatuses.

Advantageous Effects Common to First to Third Specific Functions

In the first to third specific functions, since the mobile apparatus 48 is the tablet PC, handheld computer, or PDA, the mobile apparatus 48 can be easily carried to the vicinity of the patient 16.

In particular, the tablet computer does not have keyboards, mice, or concave-convex surfaces. Therefore, the tablet computer surface can be subjected to a sterilization treatment after the surgical operation, whereby it is possible to keep the surface clean and to prevent in-hospital infection.

Furthermore, the mobile apparatus 48 is sealed in the sterilized bag 200 and used in this state, and the doctor 18 operates the mobile apparatus 48 through the sterilized bag 200. Therefore, the mobile apparatus 48 can be kept clean. In a case where the sterilized bag 200 is a disposable transparent bag, the mobile apparatus 48 can be repeatedly used after sealed in another new sterilized bag 200 without sterilizing the mobile apparatus 48.

Modifications of Embodiment

The medical system 10 of this embodiment is not limited to the above description, and may have the following structures (according to first to third modifications).

First Modification

Figure 15A:
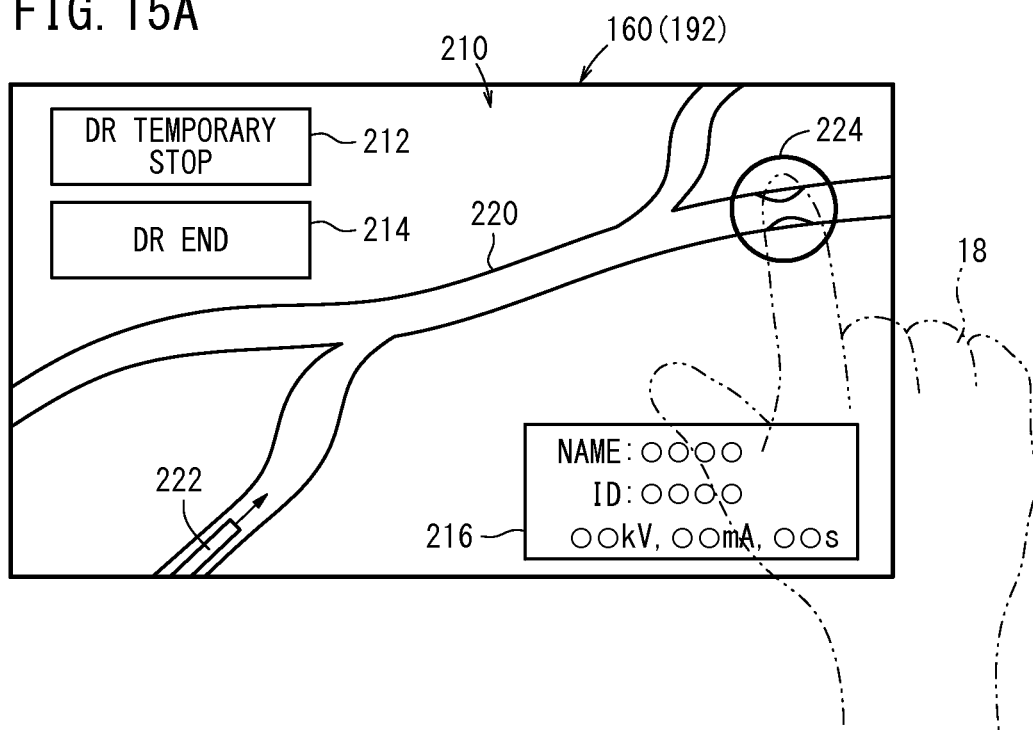
FIGS. 15A and 15B are explanatory views for illustrating a first modification of this embodiment.
Figure 15B:
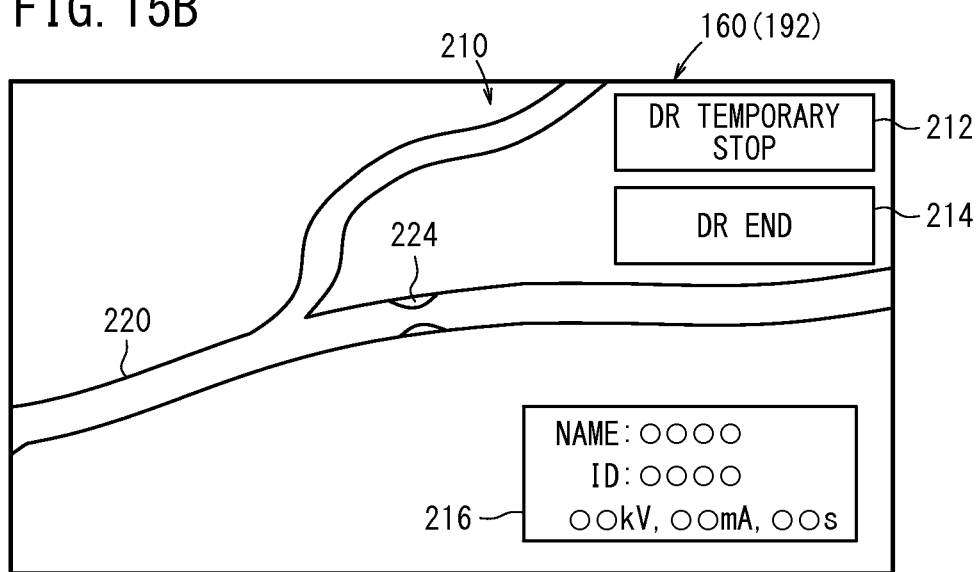

In the first modification of this embodiment, in a case where the doctor 18 clicks a desired area on the screen of the display portion 192 with a finger as shown in FIG. 15A, the next capturing of the image of the patient 16 is performed such that the clicked area is displayed in the center of the screen. Thus, in the image acquired by the next capturing, the clicked area is displayed in the center of the screen of the display portion 192 as shown in FIG. 15B. In the following description, the moving image acquired in the fluoroscopic image capturing is displayed on the screen of the display portion 192 in the same manner as FIG. 6A by way of example.

As shown in FIG. 15A, in a case where the moving fluorography image is displayed on the screen of the display portion 192 and the circled area containing the narrowed portion 224 is an area of concern 296 of the doctor 18, the doctor 18 clicks the area of concern 296 with a finger. The control portion 132 in the mobile apparatus 48 calculates the present position (height and plan position) of the radiation source 106 corresponding to the area clicked by the doctor 18 and the position of the radiation source 106 suitable for displaying the clicked area in the center of the screen based on the image capturing conditions stored in the image capturing condition storage portion 136, the radiographic image currently displayed on the display portion 192, and the like. The control portion 132 calculates the movement distance of the radiation source 106 based on the calculated positions.

Then, the control portion 132 sends a control signal indicating the movement distance of the radiation source 106 from the communication portion 130 to the control portion 108 in the radiation output apparatus 22 through the console 52. The control portion 108 receives the control signal from the control portion 132 and then acts to move the multijoint arm 42 based on the movement distance represented by the control signal. Consequently, the position of the radiation source 106 is automatically adjusted such that the clicked area is displayed in the center of the screen.

In a case where the control portion 108 receives the synchronization control signal in a state where the position of the radiation source 106 is thus adjusted, the radiation source 106 applies the radiation 20 to the imaging area of the patient 16 at a predetermined dose for a predetermined irradiation time under the image capturing conditions thereby to start the next image capturing. Thus, in a case where the radiation conversion panel 80 converts the radiation 20 transmitted through the patient 16 into the radiographic image and the mobile apparatus 48 acquires the radiographic image sent from the radiographic image capturing apparatus 24, the radiographic image (acquired in the next image capturing) with the clicked area being positioned in the center of the screen is displayed on the screen of the display portion 160 in the mobile apparatus 48 as shown in FIG. 16B.

In this case, the radiographic image with the clicked area being positioned in the center of the screen is obtained by applying the radiation 20 from the radiation source 106 to the patient 16 such that the internal site of the patient 16 corresponding to the clicked area is positioned at the center of the region irradiated with the radiation 20. Thus, in the first modification, the irradiation region (the irradiation position, the irradiation area) of the radiation 20 corresponding to the radiographic image shown in FIG. 15A is different from the irradiation region (the irradiation position, the irradiation area) of the radiation 20 corresponding to the radiographic image shown in FIG. 15B.

In the first modification, the doctor 18 just has to click the screen on the display portion 160 with a finger to automatically adjust the position of the radiation source 106 and the irradiation region of the radiation 20 such that the clicked area is positioned in the center of the screen. Further, after the adjustment, the next image capturing is performed. Therefore, in a case that a radiographic image acquired in the next image capturing is displayed on the screen of the display portion 160, the clicked area can be reliably displayed in the center of the screen.

The mobile apparatus 48 and the console 52 are switched between the master and the slave as described above. Therefore, the doctor 18 or the technician 54 may operate the operation portion 194 in the console 52 used as the master to automatically adjust the position of the radiation source 106. Also in this case, the position of the radiation source 106 and the irradiation region of the radiation 20 are automatically adjusted such that the clicked area is positioned in the center of the screen of the display portion 192. Therefore, in a case that the next image capturing is performed after the adjustment, and the radiographic image is acquired in the next image capturing, the radiographic image with the clicked are being positioned in the center of the screen can be displayed on the screen of the display portion 192.

The mobile apparatus 48 delivers the radiographic image to the mobile apparatuses 120a, 120b and the display apparatus 124 in real time via the terrestrial digital television broadcasting. Therefore, of course, the radiographic image with the clicked area being positioned in the center of the screen can be displayed on the mobile apparatuses 120a, 120b and the display apparatus 124.

Further, in the above description, the doctor 18 clicks the screen on the display portion 160 with a finger to automatically adjust the position of the radiation source 106 and the irradiation region of the radiation 20. Alternatively, the doctor 18 may operate the icon 204 shown in FIG. 5 with a finger to specify the area to be clicked. In this case, the icon 204 contains an arrow button for scrolling the screen and a decision button. The doctor 18 operates the arrow button to select the area to be clicked, and pushes the decision button to set the area to be clicked. Then, the adjustment of the position of the radiation source 106 (the adjustment of the irradiation region of the radiation 20) is started.

Still further, the position, etc. of the radiation source 106 corresponding to the clicked area is automatically calculated and adjusted by the mobile apparatus 48 or the console 52 in the above description. Alternatively, the doctor 18 or the technician 54 may use the mobile apparatus 48 or the console 52 to manually set the adjustment of the position of the radiation source 106 in the next image capturing. In this case, the doctor 18 or the technician 54 operates the icon 204 on the mobile apparatus 48 or the operation portion 162 on the console 52 to input the position (including the height position) of the radiation source 106 and the irradiation region of the radiation 20. Then, the mobile apparatus 48 or the console 52 sends a control signal indicating the input position of the radiation source 106 and the input irradiation region of the radiation 20 to the radiation output apparatus 22. The control portion 108 in the radiation output apparatus 22 receives the control signal, and acts to move the multijoint arm 42 based on the control signal to adjust the position of the radiation source 106. Furthermore, the control portion 108 acts to define the irradiation region of the radiation 20 using a collimator (not shown).

Though the position of the radiation source 106 is adjusted by the multijoint arm 42 in the above description, the position adjustment is not limited thereto. For example, in a case where the radiation source 106 is attached to the end of the multijoint arm 42, the radiation source 106 may be rotated around a shaft of the multijoint arm 42 to adjust the orientation of the radiation source 106 as desired.

In the case of adjusting the position of the radiation source 106, the radiation source 106 and the multijoint arm 42 are moved. Thus, it is preferred that the mobile apparatus 48 or the console 52 should inform (warn) the doctor 18 or the technician 54, at least during the movement thereof, that the position of the radiation source 106 is being adjusted, by displaying information indicating the adjustment on the screen of the display portion 160, 192 or by outputting a sound indicating the adjustment from a speaker (not shown). In this case, the doctor 18 or the technician 54 can be prevented from unexpectedly getting in touch with the radiation source 106 and the multijoint arm 42 under the adjustment, and from being carelessly exposed to radiation in the next image capturing.

Second Modification

In the above description, the doctor 18 operates on the patient 16 in the operating room 12.

In the second modification of this embodiment, as shown in FIG. 16, in a case where the patient 16 lies down on a bed 300 in a patient room 298 or the like in the medical institution, the technician 54 or the doctor 18 carries a round cart 302 to the patient room 298 and performs therein a diagnosis of the patient 16 (such as the radiographic image capturing using the radiation source 106 and the radiographic image capturing apparatus 24).

In the round cart 302, a base unit 306 is disposed as a housing on a dolly 304. The console 52, which has a display operation portion 308 with the display portion 192, the operation portion 194, and the exposure switch 196 being integrated thereinto, is disposed in the base unit 306. Insertion slots, into which the radiographic image capturing apparatus 24 can be inserted, are formed on the base unit 306. The cradle 28 for charging the radiographic image capturing apparatus 24 inserted into the insertion slot is disposed inside the base unit 306.

Also the mobile apparatus 48 can be inserted into the insertion slot and charged by the cradle 28. A speaker 310 for outputting a sound indicating various information is disposed on the side of the base unit 306.

A support pole 312 stands upright on the front side of the base unit 306, and the radiation output apparatus 22 is attached to the end of a support arm 314 that can be lowered and raised along the support pole 312. In this case, for example, the irradiation direction of the radiation 20 output from the radiation source 106 can be changed by rotating the radiation output apparatus 22 with respect to the end of the support arm 314. The camera 34 is disposed on the outer periphery of the radiation output apparatus 22. A collimator 316 for defining the irradiation region of the radiation 20 is disposed on the output side of the radiation 20 of the radiation output apparatus 22.

Therefore, the round cart 302 can be used for carrying the radiation output apparatus 22, the radiographic image capturing apparatus 24, the cradle 28, and the console 52 integrated with each other (not separated from each other), with the radiographic image capturing apparatus 24 and the mobile apparatus 48 being inserted into the cradle 28. In this case, the round cart 302 can be moved based on the operation on the mobile apparatus 48 or the console 52 by the technician 54 or the doctor 18. The round cart 302 can communicate with the outside (such as the RIS 112, the HIS 114, or the PACS 116) via the wireless communication link. Therefore, it is not necessary to take into account a wiring process, and the round cart 302 can be moved closer to the bed 300 (or the patient 16 lying thereon) from any side.

In FIG. 16, the radiographic image capturing apparatus 24 is interposed between the bed 300 and the patient, the patient 16 is positioned correctly with respect to the radiation source 106 and the radiographic image capturing apparatus 24, and then the technician 54 or the doctor 18 operates the mobile apparatus 48 to remotely control the radiation source 106 and the radiographic image capturing apparatus 24, whereby the radiation 20 is applied from the radiation source 106 to the patient 16.

The second modification is different from the above embodiment of FIG. 1 and the first modification in that the patient 16 stays in the patient room 298 and the console 52 can be carried using the round cart 302. Thus, the second modification has the same effects as the above embodiment and the first modification in a structure that is similar to the above embodiment and the first modification.

The structure, the processing sequence, and the advantageous effects derived therefrom in the second modification will be described below. The following explanation of the second modification overlaps partially with the explanation of the above embodiment and the first modification.

Also in the second modification, the technician 54 or the doctor 18 may operate the mobile apparatus 48 or the console 52 and click a desired area displayed on the screen of the display portion 160 and the display operation portion 308 to adjust the position of the radiation source 106 (the irradiation region of the radiation 20) in the same manner as the first modification. In a case where the next image capturing is performed at the adjusted position of the radiation source 106, with respect to the radiographic image acquired in the next image capturing, the clicked area can be displayed in the center of the screen of the display portion 160 and the display operation portion 308. In this case, the irradiation region of the radiation 20 may be defined by using the collimator 316 during the positional adjustment of the radiation source 106.

The position of the radiation source 106 and the irradiation region of the radiation 20 can be adjusted by lowering or raising the support arm 314, by rotating the radiation output apparatus 22 with respect to the support arm 314, and by moving the round cart 302 per se. In this case, it is preferable to warn the technician 54 or the doctor 18 that the position of the radiation source 106 is being adjusted and the irradiation region of the radiation 20 is being adjusted, by outputting a sound from a speaker 310, or by displaying information on the display portion 160 of the mobile apparatus 48 and the display operation portion 308. Consequently, the technician 54 or the doctor 18 can be prevented from unexpectedly getting in touch with the radiation source 106 and the round cart 302 under the adjustment, and from being carelessly exposed to radiation in the next image capturing.

Also in the second modification, the mobile apparatus 48 and the console 52 are used as the master and the slave in the same manner as the above embodiment. Therefore, it is a matter of course that, by operating the master of the mobile apparatus 48 or the console 52, the entire round cart 302 can be controlled, the image capturing conditions can be changed, and the image processings, etc. of the various images can be performed.

In the second modification, at least in a case where the round cart 302 having the console 52 and the technician 54 or the doctor 18 having the mobile apparatus 48 are away from each other, the mobile apparatus 48 is switched to the master. Thus, in the second modification, in a case where the radiation output apparatus 22, the radiographic image capturing apparatus 24, the mobile apparatus 48, and the console 52 are placed on the round cart 302, the round cart 302 is carried to the patient room 298 in which the patient 16 stays, the technician 54 or the doctor 18 then separates the mobile apparatus 48 from the round cart 302, and the technician 54 or the doctor 18 moves to a position away from the round cart 302 (a position in which the technician 54 or the doctor 18 cannot immediately operate the console 52), the mobile apparatus 48 can be switched to the master.

Specifically, in the second modification, in a case where the technician 54 or the doctor 18 having the mobile apparatus 48 is in a position away from the round cart 302 (closer to the patient 16) in order to perform the positioning of the patient 16 with respect to the radiation output apparatus 22 and the radiographic image capturing apparatus 24, the mobile apparatus 48 is switched to the master.

Therefore, in a case where the technician 54 or the doctor 18 examines the patient 16 and thereby wants to change the image capturing conditions during the positioning of the patient 16, the technician 54 or the doctor 18 can operate the mobile apparatus 48 to change the image capturing conditions without going back to the round cart 302. Thus, the technician 54 or the doctor 18 does not need to go back and forth between the patient 16 and the round cart 302 (the console 52 placed thereon) in order to change the image capturing conditions. Consequently, the workload of the technician 54 or the doctor 18 can be reduced, and the procedures including the change of the image capturing conditions and the positioning of the patient 16 can be promptly performed.

The mobile apparatus 48 may be switched to the master after the positioning of the patient 16. In this case, the technician 54 or the doctor 18 can operate the mobile apparatus 48 to remotely control the radiation source 106 and the radiographic image capturing apparatus 24. Consequently, the fluoroscopic image capturing of the patient 16 can be started, and the technician 54 or the doctor 18 can be prevented from being exposed to radiation.

The mobile apparatus 48 and the radiographic image capturing apparatus 24 may have a contact sensor (not shown).

In a case where the technician 54 or the doctor 18 holds the mobile apparatus 48 and takes the mobile apparatus 48 out of the round cart 302, the contact sensor detects the contact of the technician 54 or the doctor 18 with the mobile apparatus 48, and the mobile apparatus 48 is switched to the master based on the detection result by the contact sensor.

In a case where the technician 54 or the doctor 18 interposes the radiographic image capturing apparatus 24 between the patient 16 and the bed 300 during the positioning of the patient 16, the contact sensor detects the contact of the patient 16 with the radiographic image capturing apparatus 24, and the radiographic image capturing apparatus 24 sends the detection result by the contact sensor to the mobile apparatus 48. The mobile apparatus 48 receives the detection result and is switched to the master based on the detection result.

The mobile apparatus 48 can be switched to the master based on the detection result of the contact sensor in this manner. Consequently, the mobile apparatus 48 can be reliably made to function as the master after the positioning of the patient 16.

The round cart 302 can be moved in response to the operation on the mobile apparatus 48 or the console 52 by the technician 54 or the doctor 18 as described above. Thus, there is a case where the technician 54 or the doctor 18 carries the mobile apparatus 48 constantly. In such a case, the mobile apparatus 48 may be made to function as the master constantly only during the rounds of patients in the medical institution. Alternatively, in a case where the technician 54 or the doctor 18 carries the mobile apparatus 48 constantly, for example, in or after the positioning of the patient 16, the mobile apparatus 48 may be switched to the master based on the operation of the icon 204 on the display portion 160 by the technician 54 or the doctor 18 or based on the detection result of the contact sensor.

In the second modification, as described above, the technician 54 or the doctor 18 interposes the radiographic image capturing apparatus 24 between the patient 16 and the bed 300 and operates the mobile apparatus 48 in order to perform the radiographic image capturing on the patient 16. Furthermore, the technician 54 or the doctor 18 can operate the mobile apparatus 48 to move the round cart 302. Thus, in the second modification, the technician 54 or the doctor 18 touches at least the mobile apparatus 48 and the radiographic image capturing apparatus 24.

Therefore, in the second modification, it is preferred that at least the mobile apparatus 48 and the radiographic image capturing apparatus 24 should be each sealed in a contamination prevention bag (such as the sterilized bag 200) and used in such a sealed state in order to prevent contamination.

Conventionally, a washing treatment of wiping with alcohol has been conducted on not only the radiographic image capturing apparatus 24 but also the entire round cart 302 after the daily round. Thus, additional work is required in the washing treatment after the round, resulting in the increased workload of the technician 54.

In contrast, in the second modification, at least the mobile apparatus 48 and the radiographic image capturing apparatus 24 are sealed in the contamination prevention bags and used in such a sealed state. Therefore, the technician 54 only has to discard the contamination prevention bags used for sealing the mobile apparatus 48 and the radiographic image capturing apparatus 24 and to wash only the mobile apparatus 48 and the radiographic image capturing apparatus 24 after the round. Thus, the workload can be significantly reduced in the washing treatment after the round.

The technician 54 or the doctor 18 is unlikely to touch the components such as the round cart 302, other than the mobile apparatus 48 and the radiographic image capturing apparatus 24. Therefore, the washing of the other components can be easily carried out after the round, or the washing thereof is not required.

The contamination prevention bag may be attached and removed in the following manner. For example, the round cart 302 may be equipped with an apparatus for attaching and removing the contamination prevention bag. In a case where the technician 54 or the doctor 18 takes out the radiographic image capturing apparatus 24 from the round cart 302 in order to capture the radiographic image of the patient 16, the radiographic image capturing apparatus 24 may be automatically sealed in the contamination prevention bag by the apparatus in the taking out process. Thus, the workload of the technician 54 or the doctor 18 can be reduced in the step of sealing the radiographic image capturing apparatus 24, and the radiographic image capturing apparatus 24 can be used in the sealed state in the contamination prevention bag. In a case where the technician 54 or the doctor 18 returns the radiographic image capturing apparatus 24 to the round cart 302 after the image capturing, the contamination prevention bag may be automatically torn and collected by the apparatus.

The console 52 containing the display operation portion 308 has a keyboard, etc. Therefore, the console 52 has a concave-convex surface, and the contamination prevention bag cannot be easily attached thereto or removed therefrom. Also for this reason, it is preferred that the mobile apparatus 48 should be sealed in the contamination prevention bag and be made to function as the master, whereby the advantageous effects can be easily obtained.

The mobile apparatus 48 may act to display a table containing a list of the patients 16 to be examined in a certain day on the screen of the display portion 160 based on the order information acquired from the RIS 112 via the console 52. Therefore, the technician 54 or the doctor 18 can know in advance various information such as the number of the patients 16 to be examined, the information on the patients 16, etc.

In the image capturing in the round, the order information including the image capturing conditions are often changed depending on the state of the patient 16 in the round. As described above, the mobile apparatus 48 function as the master and has approximately the same functions as the console 52.

Therefore, the technician 54 or the doctor 18 can easily change the order information (the image capturing conditions contained therein) stored in the order information storage portion 134 by operating the mobile apparatus 48 while checking the state of the patient 16 in the round. Thus, the mobile apparatus 48 can also act as the RIS 112, and the control portion 132 can update the order information stored in the order information storage portion 134 to the changed order information. The control portion 132 sends the changed order information from the communication portion 130 to the console 52 via the wireless communication link. The console 52 updates the order information stored in the order information storage portion 176 to the received order information. Consequently, the process of capturing the radiographic image of the patient 16 is performed based on the changed order information.

In the second modification, in a case where the round cart 302 carries a plurality of the radiographic image capturing apparatuses 24, the mobile apparatus 48 may select an adequate apparatus from the radiographic image capturing apparatuses 24 based on the order information and may display the adequate apparatus on the display portion 160. Therefore, the technician 54 or the doctor 18 can take out the adequate radiographic image capturing apparatus 24 from the round cart 302 based on the information displayed on the display portion 160, and can interpose the adequate radiographic image capturing apparatus 24 between the patient 16 and the bed 300.

In the second modification, in view of preventing interference, it is preferred that the frequency range used in the wireless communication link between the mobile apparatus 48 and the console 52 should be different from the frequency range used in the wireless communication link between the radiographic image capturing apparatus 24 and the console 52.

In the second modification, there may be a patient other than the subject patient 16 in the patient room 298. In this case, in order that the other patient cannot watch the information on the patient 16, it is preferred that, in the round (particularly before the image capturing), the mobile apparatus 48 be used as the master, and the information for capturing the image of the patient 16 be displayed only on the screen of the display portion 160 in the mobile apparatus 48 used by only the technician 54 or the doctor 18. In this case, no information is displayed on the screen of the display operation portion 308 in the console 52 (the screen of the display operation portion 308 is cleared). Consequently, leakage of the information on the patient 16 to the other patients can be prevented.

In a case where the technician 54 or the doctor 18 does not look at the screen of the display portion 160, it is preferred that the technician 54 or the doctor 18 should operate the icon 204 on the display portion 160 to clear the screen. In this case, the other patients cannot readily watch the information on the patient 16, and thus the leakage of the information on the patient 16 can be prevented.

In the second modification, in the case of using the mobile apparatus 48 as the master, the mobile apparatus 48 can act to display, side-by-side, the radiographic image of the patient 16 obtained in the present capturing process together with the radiographic image of the patient 16 obtained in the past capturing process on the screen of the display portion 160. Therefore, the technician 54 or the doctor 18 can compare the both images and can easily explain to the patient 16 lying on the bed 300 about the course of the disorder, etc. The mobile apparatus 48 can access the PACS 116 using the DICOM server of the console 52 and the LAN 110. Therefore, the mobile apparatus 48 can acquire the past radiographic image from the PACS 116 via the console 52, and can easily display the acquired past radiographic image on the display portion 160.

Third Modification

Figure 17:
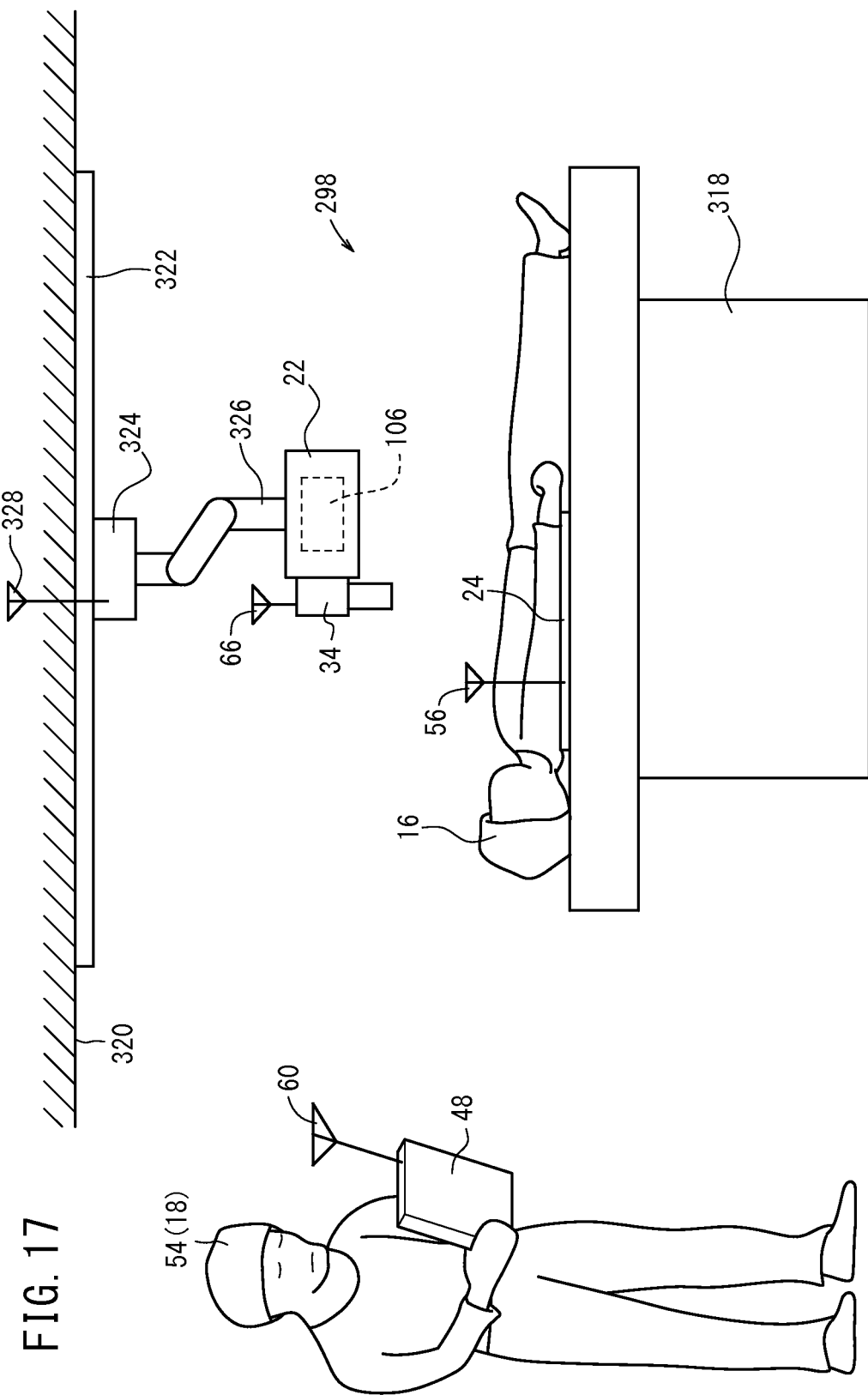
FIG. 17 is an explanatory view for illustrating a third modification of this embodiment.

In the third modification of this embodiment, the second modification (see FIG. 16) is partially modified as shown in FIG. 17.

In this modification, the patient 16 lies down on a bed 318 in the patient room 298. A straight rail 322 extends straight on the ceiling 320 of the patient room 298, and a base member 324 can be moved along the rail 322. The base member 324 is connected with a multijoint arm 326, and the radiation output apparatus 22 is attached to the end of the multijoint arm 326. The camera 34 is attached to the outer periphery of the radiation output apparatus 22. The base member 324 has an antenna 328. The base member 324 receives a control signal from the mobile apparatus 48 via a wireless communication link, and a drive mechanism (not shown) disposed in the base member 324 is actuated in response to the received control signal. Then, the base member 324 is moved along the rail 322 and acts to control the multijoint arm 326.

Thus, the structure of the third modification is approximately equal to that of the second modification except that the radiation output apparatus 22 is suspended from and supported by the ceiling.

In the third modification, the technician 54 or the doctor 18 operates the mobile apparatus 48 to change the position of the radiation source 106 and the irradiation region of the radiation 20 in the same manner as the first and second modifications. In this case, a control signal instructing to change the position of the radiation source 106 and the irradiation region of the radiation 20 is sent from the communication portion 130 in the mobile apparatus 48 to the antenna 328 via the wireless communication link. The drive mechanism is actuated based on the control signal received by the antenna 328, acts to move the base member 324 to a predetermined position along the rail 322, and acts to operate the multijoint arm 326 to adjust (the radiation source 106 of) the radiation output apparatus 22 to a predetermined height and direction. Therefore, the radiation source 106 can be moved to a desired position, and the irradiation region of the radiation 20 can be changed. Consequently, the radiation 20 can be emitted from the changed position to the patient 16 within the irradiation region in the next image capturing.

It is to be understood that the present invention is not limited to the above embodiment, and various changes and modifications may be made therein without departing from the scope of the invention.

The invention claimed is:

1. A radiographic image capturing system comprising:
a radiation source for applying radiation to a subject;
a cassette for converting the radiation transmitted through the subject into a radiographic image;
a console for remotely controlling the radiation source and the cassette, disposed away from the subject;
a mobile apparatus being a tablet computer, a handheld computer, or a personal digital assistant that can be moved close to the subject and can be used instead of the console for controlling the radiation source and the cassette; and
a switch processing portion that enables the console or the mobile apparatus to switch between a main apparatus that controls the radiation source and the cassette and a subordinate apparatus that does not control the radiation source and the cassette,
wherein the cassette contains
a first communication portion for sending signals to and receiving signals from the console via a wireless communication link,
a second communication portion for sending signals to and receiving signals from the mobile apparatus via a wireless communication link, and
an image processing portion for subjecting the radiographic image to a thinning processing to generate a thinned image,
the first communication portion sends the radiographic image to the console,
the second communication portion sends the thinned image to the mobile apparatus when the mobile apparatus is switched to the main apparatus, and
a frequency range of the wireless communication link between the mobile apparatus and the cassette is different at least from a frequency range of the wireless communication link between the control apparatus and the cassette.

2. The radiographic image capturing system according to claim 1, wherein
in a case where a fluoroscopic image capturing is started for repeatedly applying the radiation to the subject by the radiation source so as to sequentially acquire the radiographic images by the cassette, the main apparatus is switched from the console to the mobile apparatus by the switch processing portion.

3. The radiographic image capturing system according t claim 2, wherein
in a case where the fluoroscopic image capturing is ended, the main apparatus is switched from the mobile apparatus to the console by the switch processing portion.

4. The radiographic image capturing system according to claim 2, wherein
in a case where the fluoroscopic image capturing is interrupted, the mobile apparatus is maintained by the switch processing portion as the main apparatus.

5. The radiographic image capturing according to claim 1, wherein
in a case where at least the console and the mobile apparatus are disposed away from each other, the main apparatus is switched from the console to the mobile apparatus by the switch processing portion.

6. The radiographic image capturing system according to claim 5, further comprising:

a round cart for carrying at least the console, the mobile apparatus, and the cassette, wherein in a case where the mobile apparatus is separated from the round cart, the main apparatus is switched from the console to the mobile apparatus by the switch processing portion.

7. The radiographic image capturing system according to claim 6, wherein in or after a step of positioning the subject with respect to the radiation source and the cassette, the main apparatus is switched from the console to the mobile apparatus by the switch processing portion.

8. The radiographic image capturing system according to claim 1, wherein the mobile apparatus contains a touch panel, and an operator operates the touch panel to control the radiation source and the cassette.

9. The radiographic image capturing system according to claim 1, wherein the mobile apparatus is sealed in a sterilized bag and used in this state.

10. The radiographic image capturing system according to claim 1, wherein the switch processing portion is formed on at least one of the console and the mobile apparatus, and the console and the mobile apparatus can send signals to and receive signals from each other.

11. The radiographic image capturing system according to claim 1, wherein the cassette further contains an image storage portion for storing the radiographic image, and in a case where there is a defect in signal sending and receiving between the first communication portion and the console via the wired communication link, the image storage portion stores the radiographic image.

* * * * *